(12) United States Patent
Kodama et al.

(10) Patent No.: US 6,297,373 B1
(45) Date of Patent: Oct. 2, 2001

(54) METHOD FOR ACYLATING HEXAKIS (ARYLMETHYL) HEXAAZAISOWURTZITANE

(75) Inventors: Tamotsu Kodama, Kurashiki; Naoko Ishihara, Kawasaki; Haruyuki Minoura; Nobuhisa Miyake, both of Kurashiki; Setsuo Yamamatsu, Fuji, all of (JP)

(73) Assignee: Asahi Kasei Kabushiki Kaisha, Osaka (JP)

(*) Notice: Subject to any disclaimer, the term of this patent is extended or adjusted under 35 U.S.C. 154(b) by 0 days.

(21) Appl. No.: 09/508,581

(22) PCT Filed: Oct. 14, 1998

(86) PCT No.: PCT/JP98/04644

§ 371 Date: Mar. 14, 2000

§ 102(e) Date: Mar. 14, 2000

(87) PCT Pub. No.: WO99/19328

PCT Pub. Date: Apr. 22, 1999

(30) Foreign Application Priority Data

Dec. 26, 1997 (JP) .................................. 9-366728
Feb. 13, 1998 (JP) .................................. 10-046369

(51) Int. Cl.$^7$ .............................................. C07D 487/22
(52) U.S. Cl. .................................... 540/554; 540/556
(58) Field of Search .................................... 540/554, 556

(56) References Cited

U.S. PATENT DOCUMENTS 5,693,794   12/1997   Nielsen ................... 540/554
5,739,325 * 4/1998   Wardle et al. ........... 540/554

FOREIGN PATENT DOCUMENTS 8-208655      8/1996  (JP) .
WO 96/23792   8/1996  (WO) .
WO 97/20785   6/1997  (WO) .

OTHER PUBLICATIONS

A.J. Bellamy, "Reductive Debenzylation of Hexabenzyl-hexaazaisowurtzitane", Tetrahedron, vol. 51, No. 16, pp. 4711–4722, (1995).

A.T. Nielsen et al., Polyazapolycyclics by Condensation of Aldehydes with Amines. 2. Formation of 2,4,6,8,10.12–Hexabenzyl–2,4,6,8,10,12–hexaazatetracyclo [5.5.0.$^{5,9}$.0$^{3,11}$]dodecanes from Glyoxal and Benzylamines$^{1,2}$, J. Org. Chem., vol. 55, pp. 1459–1466, (1990).

* cited by examiner

Primary Examiner—Mukund J. Shah
Assistant Examiner—Venkataraman Balasubramanian
(74) Attorney, Agent, or Firm—Finnegan, Henderson, Farabow, Garrett & Dunner, L.L.P.

(57) ABSTRACT

A method for acylating a hexakis (arylmethyl) hexaazaisowurtzitane ($WB_6$) by reductively removing the arylmethyl groups in the presence of an acylating agent, characterized by contacting a $WB_6$ (a) with a heterogeneous system reduction catalyst (b) in the presence of an acylating agent (c) and a reducing agent (d) in a solvent (e) for the $WB_6$ (a) to reductively remove the arylmethyl groups from the $WB_6$ (a) and acylate the same, and by preventing the $WB_6$ (a) and the catalyst (b) from being contacted with each other when at least either of the acylating agent (c) and the reducing agent (d) is not present. In this method, the decomposition of the $WB_6$ skeleton, which readily occurs in the beginning of the acylation of the $WB_6$ as a starting material, can be highly effectively inhibited. This method can hence stably produce a tetraacylhexaazaisowurtzitane derivative in a high yield and is industrially advantageous.

4 Claims, 4 Drawing Sheets

METHOD FOR ACYLATING HEXAKIS (ARYLMETHYL) HEXAAZAISOWURTZITANE

BACKGROUND OF THE INVENTION

1. Field of the Invention

The present invention relates to a method for acylating a hexakis(arylmethyl)hexaazaisowurtzitane. More particularly, the present invention is concerned with a method for acylating a hexakis(arylmethyl) hexaazaisowurtzitane (hereinafter, frequently referred to simply as "$WB_6$") by reductive dearylmethylation in the presence of an acylating agent, which comprises contacting (a) a $WB_6$ and (b) a heterogeneous reduction catalyst with each other in the presence of (c) an acylating agent and (d) a reducing agent in (e) a solvent for the $WB_6$ (a), thereby performing a reductive dearylmethylation/acylation reaction of $WB_6$ (a), wherein there is no contact between $WB_6$ (a) and heterogeneous reduction catalyst (b) in the absence of any of acylating agent (c) and reducing agent (d). By the method of the present invention, in the production of tetraacylhexaazaisowurtzitane derivatives (which are useful as precursors of a hexanitrohexaazaisowurtzitane utilized for improving the performance of conventional explosives) from a $WB_6$ by acylation, the decomposition of a hexaazaisowurtzitane skeleton, which is likely to occur at the initial stage of the acylation reaction of a $WB_6$ as a starting material, can be very effectively suppressed, so that desired tetraacylhexaazaisowurtzitane derivatives can be stably produced in high yield. Therefore, the method of the present invention is commercially advantageous. Further, the method of the present invention is also advantageous in that the lowering of the catalytic activity of the reduction catalyst during the reaction can be effectively suppressed, as compared to the case of conventional methods.

2. Prior Art

As a conventional method for producing a tetraacylbis (arylmethyl)hexaazaisowurtzitane (hereinafter, frequently referred to simply as "$WA_4B_2$"), a method is known in which a hexakis(arylmethyl)hexaazaisowurtzitane (i.e., $WB_6$) is subjected to reductive dearylmethylation in the presence of an acylating agent, to thereby obtain a $WA_4B_2$ (see "Tetrahedron" vol. 51, No. 16, 4711–4722 (1995), International Patent Application Publication Nos. WO96/23792 and WO97/20785 and U.S. Pat. No. 5,693,794).

Further, there is also known a method in which a $WA_4B_2$ is subjected to reductive dearylmethylation, to thereby obtain a tetraacylhexaazaisowurtzitane (hereinafter, frequently referred to simply as "$WA_4H_2$")(see the above-mentioned WO96/23792).

In each of these patent and non-patent documents, the production of a $WA_4B_2$ is conducted by a method in which a starting material (i.e., $WB_6$) and other materials for the reaction (including an acylating agent, a solvent, a catalyst and the like) are charged into a reactor at a relatively low temperature (i.e., from 5 to 25° C.) to obtain a mixture, and then, hydrogen gas as a reducing agent is introduced into the reactor while maintaining the temperature of the obtained mixture at the above-mentioned relatively low temperature, followed by stirring, to thereby perform a reaction (exothermic reaction) wherein the temperature of the reaction system is elevated to a desired level (i.e., from 40 to 70° C.) by heat generated in the reaction. In this method, the $WB_6$ is subjected to reductive dearylmethylation in the presence of an acylating agent in order to effect the acylation of a $WB_6$ smoothly while preventing the skeletal decomposition of the $WB_6$. In this method, since the starting material and other materials for the reaction are charged into the reactor at a relatively low temperature, the occurrence of the thermal decomposition of the $WB_6$ skeleton can be suppressed. However, even by this method, the skeletal decomposition of the $WB_6$ cannot be satisfactorily suppressed. In addition, this method is accompanied by disadvantageous side reactions, such as a reductive side reaction in which the acyl group bonded to the hexaazaisowurtzitane skeleton as a result of the acylation of the $WB_6$ is converted to an alkyl group. Therefore, in this method, the desired product cannot be obtained in a satisfactorily high yield.

In the above-mentioned prior art technique, the reaction is started at a relatively low temperature (i.e., from 5 to 25° C.). However, instead of this technique, it is possible to start the reaction in a manner such that a reaction is started after the temperature of the mixture of the raw material and the reaction reagents is elevated to a predetermined level (i.e., from 40 to 70° C.). As an example of the method for starting the reaction after elevating the temperature of a mixture of the raw material/other materials for the reaction to a predetermined level, there can be mentioned a method in which the temperature of a mixture of a starting material (i.e., $WB_6$) and other reaction materials (including as an acylating agent, a solvent, a catalyst and the like) is elevated to a predetermined level without addition of hydrogen gas as a reducing agent to the mixture, and then, hydrogen gas is added to the mixture to thereby conduct the reaction. However, this method is disadvantageous in that the skeletal decomposition of the $WB_6$ markedly occurs, that is, the problems accompanying the above-mentioned prior art technique cannot be solved.

In addition, the above-mentioned prior art technique also has a problem in that the catalytic activity of a heterogeneous reduction catalyst (comprised of, for example, a rare metal of the platinum group) used in the reaction is likely to be lowered. Generally, it is desired that a deactivated catalyst is reactivated so as to recycle the catalyst. However, for reactivating the deactivated catalyst, it is necessary to perform a reactivation treatment which requires a cumbersome operation and a high cost. Therefore, from a commercial point of view, the recycling of the catalyst is not practical. Further, the above-mentioned problem of the lowering of the catalytic activity causes a disadvantage in that it is difficult to perform the reaction by a commercially advantageous continuous process. Therefore, it has been desired to prevent the lowering of the activity of the heterogeneous reduction catalyst during the reaction.

As mentioned above, the conventional method comprising subjecting a $WB_6$ to reductive dearylmethylation in the presence of an acylating agent has a problem in that it is difficult to stably produce tetraacylhexaazaisowurtzitane derivatives in high yield while surely preventing the decomposition of the hexaazaisowurtzitane skeleton. Further, the conventional method also has a problem in that the lowering of the catalytic activity during the reaction is likely to occur. Therefore, conventionally, it has been difficult to perform the reaction in a commercially advantageous continuous manner.

SUMMARY OF THE INVENTION

In this situation, the present inventors have conducted extensive and intensive studies with a view toward solving the above-mentioned problems accompanying the prior art. As a result, it has unexpectedly been found that, in a method for obtaining a reaction mixture containing at least one tetraacylhexaazaisowurtzitane derivative, which comprises contacting (a) hexakis(arylmethyl)hexaazaisowurtzitane (WB₆) and (b) a heterogeneous reduction catalyst with each other in the presence of (c) an acylating agent and (d) a reducing agent in (e) a solvent for WB₆ (a) to thereby perform a reductive dearylmethylation/acylation reaction of WB₆ (a), when contact between WB₆ (a) and heterogeneous reduction catalyst (b) in the absence of any of acylating agent (c) and reducing agent (d) is avoided, it becomes possible to prevent not only the decomposition of a hexaazaisowurtzitane skeleton (which is likely to occur at the initial stage of the acylation reaction of the WB₆) but also the lowering of the activity of the reduction catalyst during the reaction, so that desired tetraacylhexaazaisowurtzitane derivatives can be stably produced in high yield. The present invention is based on the above novel finding.

It is, therefore, a primary object of the present invention to provide a method for acylating a hexakis(arylmethyl) hexaazaisowurtzitane (WB₆) which can be used for stably producing tetraacylhexaazaisowurtzitane derivatives in high yield, while preventing the decomposition of a hexaazaisowurtzitane skeleton of the WB₆ (which is likely to occur at the initial stage of the acylation reaction of the WB₆), and while preventing the lowering of the activity of the reduction catalyst during the reaction.

The foregoing and other objects, features and advantages of the present invention will be apparent from the following detailed description taken in connection with the accompanying drawings and the appended claims.

DETAILED DESCRIPTION OF THE INVENTION

Figure 1:
FIG. 1 is a scanning electron microscope (SEM) photomicrograph (×200) of the crude hexabenzylhexaazaisowurtzitane obtained in Reference Example 3, wherein a washing treatment was conducted.

According to the present invention, there is provided a method for acylating a hexakis(arylmethyl) hexaazaisowurtzitane by reductive dearylmethylation in the presence of an acylating agent, the hexakis(arylmethyl) hexaazaisowurtzitane being represented by the following formula (1):

WB₆       (1)

wherein each B independently represents a C₇–C₂₁ arylmethyl group, and W represents a hexavalent hexaazaisowurtzitane residue represented by the following formula (2):

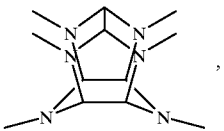

(2)

which comprises contacting (a) a hexakis(arylmethyl) hexaazaisowurtzitane and (b) a heterogeneous reduction catalyst with each other in the presence of (c) an acylating agent and (d) a reducing agent in (e) a solvent for hexakis (arylmethyl)hexaazaisowurtzitane (a), thereby performing a reductive dearylmethylation/acylation reaction of hexakis (arylmethyl)hexaazaisowurtzitane (a) to obtain a reaction mixture containing at least one tetraacylhexaazaisowurtzitane derivative, wherein there is no contact between hexakis(arylmethyl) hexaazaisowurtzitane (a) end heterogeneous reduction catalyst (b) in the absence of any of acylating agent (c) and reducing agent (d).

For an easy understanding of the present invention, the essential features and various preferred embodiments of the present invention are enumerated below.

1. A method for acylating a hexakis(arylmethyl) hexaazaisowurtzitane by reductive dearylmethylation in the presence of an acylating agent, the hexakis(arylmethyl) hexaazaisowurtzitane being represented by the following formula (1):

WB₆       (1)

wherein each B independently represents a C₇–C₂₁ arylmethyl group, and W represents a hexavalent hexaazaisowurtzitane residue represented by the following formula (2):

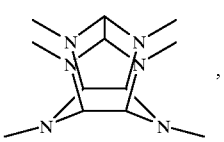

(2)

which comprises contacting (a) a hexakis(arylmethyl) hexaazaisowurtzitane and (b) a heterogeneous reduction catalyst with each other in the presence of (c) an acylating agent and (d) a reducing agent in (e) a solvent for hexakis (arylmethyl)hexaazaisowurtzitane (a), thereby performing a reductive dearylmethylation/acylation reaction of hexakis (arylmethyl)hexaazaisowurtzitane (a) to obtain a reaction mixture containing at least one tetraacylhexaazaisowurtzitane derivative, wherein there is no contact between hexakis(arylmethyl) hexaazaisowurtzitane (a) and heterogeneous reduction catalyst (b) in the absence of any of acylating agent (c) and reducing agent (d).

2. The method according to item 1 above, wherein the reductive dearylmethylation/acylation reaction of hexakis (arylmethyl)hexaazaisowurtzitane (a) is performed at 40 to 160° C.

3. The method according to item 1 or 2 above, wherein solvent (e) is an amide group-containing solvent.

4. The method according to any one of items 1 to 3 above, wherein hexakis(arylmethyl)hexaazaisowurtzitane (a) and solvent (e) are provided in the form of a solution of (a) in (e), and heterogeneous reduction catalyst (b) and reducing agent (d) are provided in the form of a mixture of (b) and (d), and wherein the solution of (a) in (e) is contacted with the mixture of (b) and (d) in the presence of acylating agent (c).

5. The method according to any one of items 1 to 3 above, wherein hexakis(arylmethyl)hexaazaisowurtzitane (a) and solvent (e) are provided in the form of a solution of (a) in (e), and heterogeneous reduction catalyst (b), acylating agent (c) and reducing agent (d) are provided in the form of a mixture of (b), (c) and (d), the mixture of (b), (c) and (d) being prepared by mixing heterogeneous reduction catalyst (b) and reducing agent (d), followed by addition of acylating agent (c) thereto, and wherein the solution of (a) in (e) is contacted with the mixture of (b), (c) and (d).

6. The method according to any one of items 1 to 5 above, wherein the reaction mixture contains at least one tetraacylhexaazaisowurtzitane, derivative represented by the following formula (3):

$$WA_4B_nH_{(2-n)} \quad (3)$$

wherein n is an integer of 0 to 2, each A independently represents a $C_1$–$C_{10}$ acyl group, H represents a hydrogen atom, and each of B and W is as defined above.

The characteristic feature of the method of the present invention resides in that the reductive dearylmethylation of a $WB_6$ is performed in the presence of an acylating agent by contacting the $WB_6$ and the heterogeneous reduction catalyst with each other under conditions wherein the contact between the $WB_6$ and the heterogeneous reduction catalyst occurs only in the presence of both of the acylating agent and the reducing agent. By virtue of this feature, the skeletal decomposition of the $WB_6$, which is likely to occur during the acylation reaction of the $WB_6$, can be very effectively suppressed.

Conventionally, it has been known that, when a $WB_6$ is subjected to reductive dearylmethylation in the absence of an acylating agent, there is formed secondary amino group-containing hexaazaisowurtzitane derivatives (such as a $WB_5H$, a $WB_4H_2$ and a $WB_3H_3$) which are structurally unstable and easily suffer decomposition of the hexaazaisowurtzitane skeleton thereof. On the other hand, it has also been known that, when a $WB_6$ is subjected to reductive dearylmethylation in the presence of an acylating agent, the above unstable, secondary amino group-containing hexaazaisowurtzitane derivatives are acylated immediately after the formation thereof to form stable, acylated hexaazaisowurtzitane derivatives, so that the decomposition of the hexaazaisowurtzitane skeleton can be suppressed. (See International Patent Application Publication No. WO96/23792.) However, it is quite unexpected that, by performing a reductive dearylmethylation reaction of the $WB_6$ in the presence of an acylating agent while avoiding contact between the $WB_6$ and the heterogeneous reduction catalyst in the absence of either or both of the acylating agent and the reducing agent, the skeletal decomposition of the $WB_6$ can be effectively suppressed, as compared to the case of the conventional methods.

In addition, by the method of the present invention, the lowering of the catalytic activity during the reaction can be effectively suppressed, as compared to the case of the conventional methods. By virtue of this effect, the method of the present invention has advantages in that the heterogeneous reduction catalyst used in the reaction can be recycled without performing a cumbersome treatment for reactivating the catalyst. In the present invention, if desired, the catalyst used in the reaction can be recycled simply by washing the catalyst to remove the solvent and other components adhered to the catalyst. (Generally, the reactivation of a deactivated heterogeneous reduction catalyst is conducted by a commercially disadvantageous operation which not only is cumbersome, but also requires a high cost. For example, in the case of a carrier-supported catalyst, when such a carrier-supported catalyst is deactivated, the reactivation thereof is conducted by, for example, a cumbersome and a high-cost method wherein the catalyst is subjected to oxidation treatment, and then, the treated catalyst is dissolved in a solvent, followed by immobilization of the catalyst on a carrier.) Further, by virtue of the above-mentioned effect of suppression of the lowering of the catalytic activity, the method of the present invention can be practiced in a commercially advantageous continuous manner.

Hereinbelow, the present invention will be described in more detail.

With respect to the synthesis method for the $WB_6$ represented by the formula (1), there is no particular limitation. However, it is preferred that the $WB_6$ used in the present invention is synthesized by subjecting an arylmethylamine and glyoxal to dehydration-condensation cyclization in the presence of an acid catalyst. With respect to the purity of the $WB_6$, it is preferred that the $WB_6$ is a high purity product having a purity of 95% or more. The use of such a high purity product is advantageous for improving the reaction rate of the reductive dearylmethylation/acylation.

In the method of the present invention, the $WB_6$ (a) represented by the formula (1) is generally used in an amount of 0.0001 to 0.4, preferably from 0.001 to 0.3, more preferably from 0.01 to 0.15, in terms of the weight ratio of the $WB_6$ (a) to the solvent (e).

It is preferred that, when the $WB_6$ is charged into a reactor, the $WB_6$ is in a form dissolved in the solvent (e). However, the $WB_6$ need not be completely dissolved in the solvent, and the $WB_6$ may be present in the solvent in the form of a slurry, in which only a part of the $WB_6$ is dissolved in the solvent. It is preferred to use a solution in which the $WB_6$ is completely dissolved in the solvent.

With respect to the reaction solvent (e) used in the method of the present invention, there is no particular limitation as long as this solvent does not adversely affect the reaction. Particularly, an amide group-containing organic solvent is preferred for improving the reaction rate and the yield of tetraacylhexaazaisowurtzitane derivatives. Examples of amide group-containing organic solvents include N,N-dimethylacetamide, N,N-dimethylformamide, 1,3-dimethyl-2-imidazolidone, N-methyl-2-pyrrolidone and the like. Among these solvents, N,N-dimethylacetamide and N,N-dimethylformamide are preferred. The above-mentioned solvents can be used individually or in combination.

In the method of the present invention, as the reducing agent (d), hydrogen gas is generally employed.

The reducing agent (d) is used generally in an amount of from 0.67 to 10,000, preferably from 0.67 to 1,000, more preferably from 2 to 50, in terms of the molar ratio of the reducing agent to the arylmethyl groups of the $WB_6$. When hydrogen gas is used as the reducing agent (d), the reaction pressure is generally in the range of from 0.001 to 100 kgf/cm², preferably 0.01 to 30 kgf/cm², more preferably 0.01 to 10 kgf/cm², most preferably 2 to 5 kgf/cm², in terms of the hydrogen partial pressure. When hydrogen gas is used as the reducing agent (d), the reaction can satisfactorily progress even when the reaction pressure (hydrogen partial pressure) is 10 kgf/cm² or less. However, when use is made of reaction equipment having a structure wherein the rate of hydrogen diffusion in the reactor and the rate of hydrogen dissolution into a reaction solution become low (for example, when using an autoclave), a high hydrogen pressure (up to about 50 kgf/cm$^2$) may be employed so as to maintain the hydrogen diffusion rate and the hydrogen dissolution rate at a high level. In addition to the hydrogen gas, inert gases such as nitrogen, argon and helium gases, may be present in the reaction system.

With respect to the heterogeneous reduction catalyst (b) used in the method of the present invention, there is no particular limitation as long as it is capable of advancing the reductive dearylmethylation of the WB$_6$ and it remains in the heterogeneous state in the solvent (e). As the heterogeneous reduction catalyst (b), a catalyst containing a metal belonging to the platinum group or containing a derivative thereof is generally used. Preferred examples of heterogeneous reduction catalysts include Pd compounds (such as Pd(OAc)$_2$, PdCl$_2$, Pd(NO$_3$)$_2$, PdO, Pd(OH)$_2$, Pd$_3$Pb and Pd$_3$Te), Pd alloys and metallic Pd; and Ru compounds (such as RuCl$_3$), Ru alloys and metallic Ru. Of these, Pd compounds (such as Pd(OAc)$_2$ and PdCl$_2$), Pd alloys and metallic Pd are more preferred. Among the above-mentioned catalysts, it is possible that some catalysts become homogeneous during the reaction, depending on the type of solvent employed. With respect to such a catalyst, it is preferred that, before use, the catalyst is caused to take a form which is unlikely to dissolve in the solvent employed, that is, the catalyst is subjected to reduction treatment after being carried on a carrier. Examples of carriers include activated carbon, silica, alumina, silica-alumina, zeolite, activated clay, zirconia and titania. Among these carriers, activated carbon is especially advantageous because it has low reactivity with a carboxylic acid derived from the acylating agent in the reaction system, and it also has relatively low reactivity with other chemical substances. In addition, for improving the catalytic activity, it is preferred that the catalyst is subjected to reduction treatment prior to use in the reductive dearylmethylation reaction. As the reducing agent for performing the reduction treatment, hydrogen gas, hydrazine or formaldehyde is preferred. When the use of a catalyst carried on a carrier is intended, the surface of the carrier may be treated so as to inactivate acid sites present on the surface of the carrier by silylation, acylation or the like, so as to activate acid sites present on the surface of the carrier by an activation treatment (such as stirring in nitric acid), or so as to neutralize the acid sites on the surface of the carrier by adsorbing an alkaline substance (e.g., NaOH). With respect to each of these treatments for modifying the acid sites on the surface of the carrier, it can be performed either before or after supporting the catalyst on the carrier.

It is preferred that the heterogeneous reduction catalyst (b) is used in the form of a slurry obtained by dispersing the catalyst in a liquid, such as a dispersion medium. There is no particular limitation with respect to the dispersion medium for preparing the slurry of catalyst (b), but a solvent which is the same as the solvent (e) is preferably used.

With respect to the acylating agent (c) used in the method of the present invention, there is no particular limitation as long as it is capable of acylating a secondary amino group to form an N-acyl bond. In general, an acylating agent such as carboxylic anhydrides, such as acetic anhydride, propionic anhydride, formic anhydride, lactic anhydride and an anhydride of a mixture of acetic acid and formic acid, is used. These carboxylic anhydrides can be used individually or in combination. Alternatively, the above-mentioned carboxylic anhydrides can be used in combination with carboxylic esters of N-hydroxysuccinimide and/or acylimidazoles. Examples of the carboxylic esters of N-hydroxysuccinimide include N-acetoxysuccinimide, N-propionyloxysuccinimide and N-(2-phenylacetoxy) succinimide; and examples of the acylimidazoles include acetylimidazole and propionylimidazole. Among these acylating agents, it is preferred to use carboxylic anhydrides alone, and a most preferable carboxylic anhydride is acetic anhydride. Further, when the acylating agent used is a liquid (such as acetic anhydride, propionic anhydride, an anhydride of a acetic acid/formic acid mixture, such acylating agent can also be used as a solvent.

The acylating agent (c) is used generally in an amount of from 0.67 to 50, preferably from 0.67 to 5, more preferably from 0.67 to 2, in terms of the molar ratio of the acylating agent to the arylmethyl groups of the WB$_6$ (a).

The reaction temperature for the reductive dearylmethylation/acylation of the WB$_6$ in the method of the present invention is generally within the range of from 40 to 160° C., preferably from 40 to 100° C., more preferably from 40 to 80° C., still more preferably from 50 to 80° C., and most preferably from 50 to 70° C. When this reaction is conducted at a relatively low temperature, namely 40° C. to less than 80° C., the conversion rate of the WB$_6$ becomes relatively low, but the thermal decomposition of the WB$_6$ skeleton can be suppressed. Therefore, it is preferable to conduct the reductive dearylmethylation/acylation at a relatively low temperature (40° C. to less than 80° C. When the reaction is conducted at a relatively high temperature, namely 80 to 160° C., even though the chemical decomposition of the WB$_6$ skeleton during the dearylmethylation/ acylation of the WB$_6$ is suppressed by the method of the present invention, the thermal decomposition of the WB$_6$ skeleton is promoted, and therefore, it becomes necessary to increase the conversion rate of the WB$_6$. In this case, there is an advantage in that the solubility of the WB$_6$ increases at a high temperature, thereby enabling the reaction to proceed at a relatively high concentration of the WB$_6$; however, from the viewpoint of suppressing the thermal decomposition of the WB$_6$, it is preferred that reaction at a high temperature of 80 to 160° C. is avoided. The reaction pressure for the reductive dearylmethylation/acylation in the method of the present invention is generally within the range of from 0.001 to 100 kgf/cm$^2$, preferably from 0.01 to 30 kgf/cm$^2$, more preferably from 0.01 to 10 kgf/cm$^2$, most preferably from 2 to 5 kgf/cm$^2$, as expressed in terms of the hydrogen partial pressure. There is no particular limitation with respect to the reaction time for the reductive dearylmethylation/acylation in the method of the present invention as long as the desired tetraacylhexaazaisowurtzitane derivatives are obtained. However, in general, a reaction time of 10 hours or less is satisfactory.

As a method for increasing the conversion rate of WB$_6$ in the reductive dearylmethylation/acylation reaction, there can be mentioned, for example, a method in which the amount of reducing agent and/or of catalyst is increased and a method in which the reaction temperature is elevated. In the method of the present invention, it is most preferred that the reaction rate is adjusted by increasing or decreasing the amount of the catalyst. The amount of the catalyst greatly varies, depending on the catalytic activity thereof, but is generally from 0.0001 to 1.0, preferably from 0.01 to 0.8, more preferably from 0.1 to 0.4, in terms of the weight ratio of the catalyst to the WB$_6$ used.

If desired, an acid type promoter may be used as a reaction promoter. Examples of acid type promoters include organic acids, such as carboxylic acids and phenols, and bromine (Br)-containing acid type promoters. Among these promoters, organic acids have low ability to cause skeletal decomposition of WB$_6$, but have low promoting effect for the reductive dearylmethylation/acylation reaction. On the other hand, a Br-containing acid type promoter has a high promoting effect for the reductive dearylmethylation/acylation reaction and a relatively low ability to cause skeletal decomposition of WB$_6$. Therefore, a Br-containing acid type promoter is preferred to an organic acid. Examples of Br-containing acid type promoters include HBr and a substance which produces HBr upon undergoing a hydrogenation reaction. More specifically, the "substance which produces HBr upon undergoing a hydrogenation reaction" is a substance having properties such that it exists in an aprotic form when it is charged into the reactor, and that it produces HBr upon being hydrogenated by a heterogeneous reduction catalyst in a reductive atmosphere (an atmosphere of hydrogen). Examples of substances which produce HBr upon undergoing a hydrogenation reaction include phenyl bromide, benzyl bromide, acetyl bromide and bromine (Br$_2$). Since a Br-containing acid type promoter has the ability to cause decomposition of WB$_6$, from the view-point of suppression of skeletal decomposition of WB$_6$, which is the objective of the present invention, it is preferred not to employ a Br-containing acid type promoter.

For suppressing the skeletal decomposition of WB$_6$, it is important to convert WB$_6$ (which is unstable to heat and acid) to an acylated hexaazaisowurtzitane compound (which is stable to heat and acid) as rapidly as possible. When two nitrogen atoms in the skeleton of WB$_6$ have been acylated, the resultant acylated hexaazaisowurtzitane derivative is caused to have extremely high stability to heat and acid, as compared to the stability of WB$_6$. For increasing both the reaction rate of the reductive dearylmethylation of WB$_6$ and the acylation rate of WB$_6$, it is preferred that the reaction is conducted at a relatively high temperature. For promoting the reaction of the acylating agent used in the method of the present invention, it is preferred to select a reaction temperature of 40° C. or more. However, since the skeletal decomposition of WB$_6$ becomes large at a temperature of more than 160° C., it is preferred that the reaction temperature is selected within the range of from 40 to 160° C. In the method of the present invention, it is preferred to adjust the reaction conditions so that the reaction temperature is within the range of from 40 to 160° C. when WB$_6$ contacts the heterogeneous reduction catalyst, or that a reaction temperature within the range of from 40 to 160° C. is achieved immediately after WB$_6$ contacts the heterogeneous reduction catalyst.

When a relatively high reaction temperature (from 40 to 160° C.) is employed for converting WB$_6$ at a high rate, it is preferred to employ an amide group-containing solvent as the reaction solvent. An amide group-containing organic solvent is preferred, because it is weakly basic and hence can neutralize an acidic proton produced by the acylation as a by-product. That is, an amide group-containing organic solvent can maintain the reaction system at around the neutral point, thereby suppressing the skeletal decomposition of WB$_6$ by an acidic proton even within a high temperature region. Further, the basicity of the amide group-containing solvent promotes acylation of WB$_6$. The reason for this is as follows. A secondary amine produced by the reductive dearylmethylation reaction of WB$_6$ is unstable, so that the secondary amine is likely to cause decomposition of the hexaazaisowurtzitane skeleton unless the skeleton is immediately protected by the acylation of the secondary amine. Since the amide group-containing solvent (which is weakly basic) promotes the acylation of the secondary amine, skeletal decomposition of WB$_6$ can be suppressed by the amide group-containing solvent. The reaction rate of the reductive dearylmethylation/acylation reaction of WB$_6$ in the method of the present invention becomes higher when the heterogeneous reduction catalyst is already in a reduced state before the start of the reaction. Therefore, it is most preferred to use a heterogeneous reduction catalyst which has been subjected to a pretreatment for reduction. As a reduction method for the heterogeneous reduction catalyst, a method in which the heterogeneous reduction catalyst is contacted with a reducing agent is employed. With respect to the reducing agent used in the reduction method, there is no particular limitation as long as it has a reducing ability. Examples of reducing agents include hydrogen gas, formic acid, hydrazine, an alcohol, an aldehyde and the like. Among these reducing agents, hydrogen gas is preferred. The reason for this resides not only in that hydrogen gas has a high reducing ability, but also in that, after the reduction treatment with hydrogen gas, there is no need for washing the reduced catalyst, and the reduced catalyst as such can be used in the method of the present invention.

As examples of methods for contacting the hexakis(arylmethyl)hexaazaisowurtzitane (a) and the heterogeneous reduction catalyst (b) with each other in the presence of the acylating agent (c) and the reducing agent (d) in the solvent (e) while satisfying the requirement defined in the present invention (that is, the requirement that there be no contact between the WB$_6$ (a) and the heterogeneous reduction catalyst (b) in the absence of any of the acylating agent (c) and the reducing agent (d)), the following methods (A) to (H) can be mentioned:

(A) a method in which the hexakis(arylmethyl)hexaazaisowurtzitane (a) and the solvent (e) are provided in the form of a solution of (a) in (e), and the heterogeneous reduction catalyst (b) and the reducing agent (d) are provided in the form of a mixture of (b) and (d), wherein the solution of (a) in (e) is contacted with the mixture of (b) and (d) in the presence of the acylating agent (c);

(B) a method in which the hexakis(arylmethyl)hexaazaisowurtzitane (a) and the solvent (e) are provided in the form of a solution of (a) in (e), and the heterogeneous reduction catalyst (b), the acylating agent (c) and the reducing agent (d) are provided in the form of a mixture of (b), (c) and (d), the mixture of (b), (c) and (d) being prepared by mixing the heterogeneous reduction catalyst (b) and the reducing agent (d), followed by addition of the acylating agent (c) thereto, wherein the solution of (a) in (e) is contacted with the mixture of (b), (c) and (d);

(C) a method in which the hexakis(arylmethyl)hexaazaisowurtzitane (a), the heterogeneous reduction catalyst (b), the acylating agent (c), the reducing agent (d) and the solvent (e) are contacted with one another simultaneously;

(D) a method in which the acylating agent (c), the reducing agent (d) and the solvent (e) are provided in the form of a mixture of (c), (d) and (e), and the hexakis(arylmethyl)hexaazaisowurtzitane (a) and the heterogeneous reduction catalyst (b) are separately introduced into the mixture of (c), (d) and (e) so as to contact (a) and (b) with each other in the presence of the mixture of (c), (d) and (e);

(E) a method in which the heterogeneous reduction catalyst (b), the acylating agent (c), the reducing agent (d) and the solvent (e) are provided in the form of a mixture of (b), (c), (d) and (e), and the hexakis(arylmethyl)hexaazaisowurtzitane (a) is contacted with the mixture of (b), (c), (d) and (e);

(F) a method in which the hexakis(arylmethyl)hexaazaisowurtzitane (a), the acylating agent (c), the reducing agent (d) and the solvent (e) are provided in the form of a mixture of (a), (c), (d) and (e), and the heterogeneous reduction catalyst (b) is contacted with the mixture of (a), (c), (d) and (e);

(G) a method in which the heterogeneous reduction catalyst (b), the reducing agent (d) and the solvent (e) are provided in the form of a mixture of (b), (d) and (e), and the hexakis(arylmethyl)hexaazaisowurtzitane (a) and the acylating agent (c) are provided in the form of a mixture of (a) and (c), wherein the mixture of (b), (d) and (e) is contacted with the mixture of (a) and (c); and (H) a method in which the hexakis(arylmethyl) hexaazaisowurtzitane (a), the reducing agent (d) and the solvent (e) are provided in the form of a mixture (a), (d) and (e), and the heterogeneous reduction catalyst (b) and the acylating agent (c) are provided in the form of a mixture of (b) and (c), wherein the mixture of (a), (d) and (e) is contacted with the mixture of (b) and (c).

Of these methods, (A), (B) and (G) are preferred.

In any of the above-mentioned methods (A) to (H), the above-mentioned contact is generally conducted in a reactor. For example, in the method (A), the mixture of (b) and (d) is obtained by introducing the reducing agent (d) (in a manner described below) into a reactor containing the heterogeneous reduction catalyst (b) charged therein, and then a solution obtained by dissolving the hexakis (arylmethyl)hexaazaisowurtzitane (a) and the acylating agent (c) in the solvent (e) is added to the above-obtained mixture of (b) and (d).

With respect to each of the above-mentioned methods (A) to (H), it is preferred that the condition that the temperature of the mixture of (a), (b), (c), (d) and (e) should be at 40 to 160° C. and under a pressure of 0.001 to 100 kgf/cm² (hydrogen partial pressure is satisfied upon completion of the preparation of the mixture of (a), (b), (c), (d) end (e) or satisfied as soon as possible (for example, within about 10 minutes) after completion of the preparation of the above-mentioned mixture.

The reaction mixture obtained by the method of the present invention comprises at least one tetraacylhexaazaisowurtzitane derivative, the heterogeneous reduction catalyst (b), the reducing agent (d) and the solvent (e). The reaction mixture may also contain a small amount of the acylating agent (c).

At least one tetraacylhexaazaisowurtzitane derivative contained in the reaction mixture obtained by the method of the present invention is generally represented by the following formula (3):

$$WA_4B_NH_{(2-n)} \quad (3)$$

wherein n is an integer of 0 to 2, each A independently represents a $C_1$–$C_{10}$ acyl group, H represents a hydrogen atom, and each of B and W is as defined above.

Examples of tetraacylhexaazaisowurtzitane derivatives represented by the formula (3) include tetraacylbis (arylmethyl)hexaazaisowurtzitane ($WA_4B_2$), tetraacylarylmethylhexaazaisowurtzitane ($WA_4BH$) and tetraacyl-hexaazaisowurtzitane ($WA_4H_2$). $WA_4B_2$ is converted to $WA_4H_2$ through $WA_4BH$ in accordance with a further progression of the reductive dearylmethylation reaction.

Of these three tetraacylhexaazaisowurtzitane derivatives, $WA_4H_2$ is especially useful as a precursor of hexanitro-hexaazaisowurtzitane. With respect to the method for nitrating $WA_4H_2$, reference can be made to, for example, WO96/23792.

Also, $WA_4B_2$ can be converted to hexanitrohexaazaisowurtzitane by nitration according to the conventional method (see, for example, WO97/20785).

With respect to the formation ratios of the above-mentioned three tetraacylhexaazaisowurtzitane derivatives, desired formation ratios can be easily achieved by appropriately adjusting the reaction rate and the reaction time. The reaction rate can be adjusted by changing the amount of the reducing agent, the reaction temperature and the activity of and the amount of the catalyst used. The reaction rate can be most effectively adjusted by changing the activity of and the amount of the catalyst.

The reaction rate has an especially great influence on reductive dearylmethylation of $WA_4B_2$. When the reaction is conducted under conditions wherein the reaction rate is low, the production ratio of $WA_4B_2$ becomes high. Whereas, when the reaction is conducted under conditions wherein the reaction rate is high, the production rate of $WA_4H_2$ becomes high. Further, when the reaction time is prolonged, the production ratio of $WA_4H_2$ is increased.

For example, when the reaction is conducted under conditions under which, 1 hour after the start of the reaction, the total weight of $WB_6$, $WAB_5$, $WA_2B_4$ and $WA_3B_3$ in the reaction system becomes 10% or less, based on the total weight of all hexaazaisowurtzitane derivatives in the reaction system (such conditions can be achieved by using, as the heterogeneous reduction catalyst (b), a 10% Pd-C in an amount of about 20% by weight, based on $WB_6$), the yields of $WA_4B_2$, $WA_4BH$ and $WA_4H_2$ as obtained 1 hour after the start of the reaction become about 60%, about 15% and about 10%, respectively. Further, when the reaction is conducted for 4 hours under the above-mentioned conditions, the yields of $WA_4B_2$, $WA_4BH$ and $WA_4H_2$ become about 10%, about 5% and about 70%, respectively.

When it is desired to obtain $WA_4H_2$ alone as the at least one tetraacylhexaazaisowurtzitane derivative represented by the formula (3), the reaction is conducted at a high reaction rate for a long time. Specifically, for example, when the reaction is conducted for 5 to 6 hours under conditions under which the total weight of $WB_6$, $WAB_5$, $WA_2B_4$ and $WA_3B_3$ becomes 10% or less, based on the total weight of all hexaazaisowurtzitane derivatives in the reaction system within 1 hour after the start of the reaction (such conditions can be achieved by using, as the heterogeneous reduction catalyst (b), a 10% Pd-C in an amount of about 20% by weight or more, based on $WB_6$), $WA_4H_2$ alone can be obtained as the at least one tetraacylhexaazaisowurtzitane represented by the formula (3).

On the other hand, when it is desired to obtain $WA_4B_2$ alone as the at least one tetraacylhexaazaisowurtzitane derivative represented by the formula (3), the reaction is conducted at a low reaction rate, for example, by using a catalyst having a low catalytic activity. Specifically, for example, when the reaction is conducted under conditions under which it takes 6 hours or more to cause the total weight of $WB_6$, $WAB_5$, $WA_2B_4$ and $WA_3B_3$ to be 10% or less, based on the total weight of all hexaazaisowurtzitane derivatives in the reaction system (such conditions can be achieved by using a catalyst having a very low catalytic activity), reductive dearylmehylation of the $WA_4B_2$ produced does almost not occur, and therefore $WA_4B_2$ alone can be obtained as the at least one tetraacylhexaazaisowurtzitane derivative represented by the formula (3).

The produced $WA_4H_2$ can be separated from the reaction mixture as follows. After completion of the reaction, water (which is a good solvent for a $WA_4H_2$) is added to the resultant reaction mixture so as to dissolve the $WA_4H_2$ in the water, and then, the heterogeneous reduction catalyst (b) is separated from the reaction mixture, to thereby obtain a liquid mixture. Then, the obtained liquid mixture is subjected to distillation to remove the water, to thereby deposit crystals of a high purity $WA_4H_2$ (hereinafter, this process is referred to as "distillative crystal deposition process").

Therefore, in the method of the present invention, it is preferred that heterogeneous reduction catalyst (b) is separated form the reaction mixture (containing $WA_4H_2$) obtained by the reaction, to thereby obtain a liquid mixture containing no catalyst but containing solvent (e), the $WA_4H_2$ and water, and then, the obtained liquid mixture is subjected to distillation to remove the water, thereby depositing crystals (distillative crystal deposition) of the tetraacylhexaazaisowurtzitane ($WA_4H_2$).

The most characteristic feature of the distillative crystal deposition process resides in that crystals of a high purity $WA_4H_2$ can be deposited in high yield simply by removing by distillation, from the reaction mixture, components (such as water and arylmethane) having a boiling point lower than that of the solvent (such as an amide group-containing solvent).

$WA_4H_2$ to be subjected to crystal deposition is almost insoluble in an ordinary organic solvent, but can be easily dissolved in a protonic highly polar solvent, such as water and carboxylic acids, differing from hexaazaisowurtzitane derivatives other than $WA_4H_2$ and skeletal decomposition products of the hexaazaisowurtzitane skeleton, wherein these other hexaazaisowurtzitane derivatives and skeletal decomposition products are contained in the solvent as impurities. Utilizing this property of $WA_4H_2$, water used as a good solvent for the desired $WA_4H_2$ is removed by distillation from a mixed solvent of water and an ordinary organic solvent to deposit crystals of the desired $WA_4H_2$, and the deposited crystals are isolated from the mixed solvent by dissolving the above-mentioned impurities in an ordinary organic solvent (e.g., an amide group-containing solvent). Thus, a high purity $WA_4H_2$ can be obtained.

With respect to the liquid mixture used in the above-mentioned distillative crystal deposition process, $WA_4H_2$ need not be completely dissolved in the liquid mixture and the $WA_4H_2$ may be present in a partially insoluble form (i.e., in the form of a slurry). However, it is preferred that the liquid mixture which contains no solids is used in the above-mentioned distillative crystal deposition process.

With respect to the distillation pressure used in the above-mentioned distillative crystal deposition process for distilling the good solvent (water) for $WA_4H_2$ (the good solvent corresponds to "first solvent" described in the Examples below), either the atmospheric pressure or the reduced pressure can be employed. With respect to the distillation temperature, there is no particular limitation as long as the good solvent can be distilled under the pressure conditions specified for the distillation. For completing the distillation within a short period of time, it is preferred to perform the distillation under the reduced pressure specified for the distillation and at a temperature which is equal to or higher than the boiling point of the good solvent as measured under the specified reduced pressure. Further, it is more preferred to perform the distillation under the reduced pressure specified for the distillation and at a temperature which is equal to or higher than the boiling point of the good solvent and which is equal to or lower than the boiling point of the poor solvent (which corresponds to "second solvent" described in the Examples below), wherein each of the boiling points of the good and poor solvents is as measured under the specified reduced pressure. When the distillation is conducted under such pressure and temperature conditions, it becomes possible to separate the good solvent from the poor solvent in this purifying process, so that each of the good solvent and poor solvent can be easily recycled. The distillation is conducted under a pressure in the range of from 0.0000001 to 760 mmHg. The smaller the pressure, the less the time required for the distillation and the lower the temperature required for carrying out the distillation, so that it becomes advantageously possible to reduce or suppress the occurrence of the thermal decomposition of the $WA_4H_2$ and hydrolysis of solvent (e)(e.g., an amide-group containing solvent). Therefore, it is preferred to perform the distillation under a reduced pressure of 200 mmHg or lower.

In the method of the present invention, when the distillative crystal deposition process is employed, some of the poor solvent may also be distilled when the good solvent is removed by distillation, as long as about 10% by weight or more of the poor solvent present in the original liquid mixture is left unremoved. Further, complete removal of the good solvent from the liquid mixture is not necessary. In fact, depending on the type of the good solvent and the type of the poor solvent, it is very difficult to completely remove the good solvent from the poor solvent in a commercial scale practice of the distillation. Therefore, in the distillative crystal deposition process, distillation may be conducted until the amount of the good solvent remaining in the resultant distillation residue becomes 0.2 or less in terms of the weight ratio of the good solvent remaining in the poor solvent to the poor solvent. For obtaining the desired compound in high yield, it is preferred to conduct the distillation until the amount of the good solvent remaining in the poor solvent becomes 0.02 or less in terms of the weight ratio of the good solvent to the poor solvent.

The method for separating the $WA_4H_2$ by filtration after the distillative crystal deposition process is briefly explained below.

A slurry containing $WA_4H_2$ as a main solid component and solvent (e) (e.g., an amide group-containing solvent) as a main liquid component, which is obtained in the distillative crystal deposition process, is subjected to filtration by means of a material or apparatus capable of filtering the slurry.

Representative examples of filtration methods include a method in which filtration is performed using a filter paper, a membrane filter or a sintered metal. Among these filtration methods, a method is appropriately selected in accordance with the particle diameter of the deposited crystals of the $WA_4H_2$. Filters having different pore diameters may be used in combination in a multistage filtration system.

Separation of the produced $WA_4B_2$ from the reaction mixture can be conducted, for example, as follows. When an amide group-containing solvent is used as reaction solvent (e), the produced $WA_4B_2$ is soluble in reaction solvent (e). Therefore, the produced $WA_4B_2$ can be separated by a method in which the heterogeneous reduction catalyst is filtered off from the reaction mixture to thereby obtain a filtrate, and then, the obtained filtrate is subjected to distillation so as to remove solvent (e), to thereby obtain $WA_4B_2$ in a solid form. In addition, when the $WA_4B_2$ is present in the reaction mixture in such a high concentration that the $WA_4B_2$ is spontaneously deposited, the $WA_4B_2$ can be separated by a method in which a good solvent for the $WA_4B_2$ is added to the reaction mixture so as to dissolve the deposited $WA_4B_2$ therein, and the heterogeneous reduction catalyst is filtered off from the reaction mixture, followed by removal of the solvent from the resultant filtrate by distillation, thereby obtaining $WA_4B_2$ in a solid form. Examples of good solvents for $WA_4B_2$ include amide group-containing solvents, such as N,N-dimethylacetamide, N,N-dimethylformamide, 1,3-dimethyl-2-imidazoline and N-methyl-2-pyrrolidone; carboxylic acids, such as formic acid, acetic acid and propionic acid; amines, such as triethylamine and ethyldimethylamine; and halogen-containing solvents, such as chloroform, dichloromethane, carbon tetrachloride and phenyl bromide.

In the method of the present invention, tetraacylhexaazaisowurtzitane ($WA_4H_2$), which is one of the tetraacylhexaazaisowurtzitane derivatives of formula (3) and which is especially advantageous as a precursor of hexanitrohexaazaisowurtzitane, can be obtained by performing the above-mentioned reductive dearylmethylation/acylation reaction to obtain at least one tetraacylhexaazaisowurtzitane derivative of formula (3) under the above-mentioned reaction conditions (temperature and pressure) until about 100% of the hexaazaisowurtzitane derivatives formed in the reaction system are converted to the $WA_4H_2$.

However, for increasing the production rate of the $WA_4H_2$, it is preferred that the reaction temperature is elevated when the total weight of the $WB_6$, the $WAB_5$, the $WA_2B_4$ and the $WA_3B_3$, which are formed in the reaction system, becomes 10% or less, preferably 0%, based on the total weight of all of the hexaazaisowurtzitane derivatives present in the reaction system, to thereby perform a reductive dearylmethylation of the tetraacylhexaazaisowurtzitane derivatives formed in the reaction system. That is, in the present invention, the high rate production of the $WA_4H_2$ becomes possible by a method in which the reductive dearylmethylation reaction of the $WB_6$ of formula (1) is performed at a relatively mild temperature (for example, at 40 to less than 80° C.) to thereby obtain a reaction mixture containing tetraacylhexaazaisowurtzitane derivatives of formula (3), and then, the reaction temperature is elevated (to, for example, 80 to 160° C.) to thereby perform a reductive dearylmethylation of the tetraacylhexaazaisowurtzitane derivatives. Hereinafter, for convenience sake, the above-mentioned reductive dearylmethylation/acylation reaction performed at a relatively mild temperature is frequently referred to as a "first-stage reaction," and the subsequent reductive dearylmethylation reaction performed at a higher reaction temperature is frequently referred to as a "second-stage reaction." In the above-mentioned method, for the reason described below, it is preferred that water is added to the reaction system at one or more points in time before and during the second-stage reaction (preferably, before the start of the second-stage reaction).

That is, in the method of the present invention, it is preferred that the reaction mixture (containing at least one tetraacylhexaazaisowurtzitane derivative) obtained by the first-stage reaction is provided as a reductive dearylmethylation reaction system, and the reductive dearylmethylation reaction system is heated to and maintained at a temperature of from 80 to 160° C. while maintaining the amount of the reducing agent present in the reductive dearylmethylation reaction system at a level of the stoichiometric amount or more, preferably considerably more than the stoichiometric amount, for reducing the at least one tetraacylhexaazaisowurtzitane derivative, wherein water is added to the reaction system at one or more points in time before and during the second-stage reaction, thereby obtaining a reaction mixture containing tetraacylhexaazaisowurtzitane represented by the following formula (4):

$WA_4H_2$              (4)

wherein each of A, H and W is as defined above.

Examples of specific methods for practicing the above-mentioned preferred mode of the method of the present invention which comprises the first-stage reaction and the second-stage reaction (hereinafter, this preferred mode is referred to simply as a "first-stage/second-stage reaction mode") include the following methods (1) to (5):

(1) a method in which, after the first-stage reaction, in situ, the second-stage reaction is performed using the same reactor as used in the first-stage reaction;

(2) a method in which, after the first-stage reaction, the reaction mixture obtained by the first-stage reaction is transferred to a reactor different from that used in the first-stage reaction, and the second-stage reaction is performed in this different reactor (in method (2), the heterogeneous reduction catalyst contained in the reaction mixture obtained by the first-stage reaction may be separated and recovered from the reaction mixture by filtration or the like, and a fresh heterogeneous reduction catalyst may be added to the resultant mixture);

(3) a method in which the first-stage reaction or the second-stage reaction is performed in a continuous manner;

(4) a method in which each of the first-stage reaction and the second-stage reaction is performed in a continuous manner, wherein the reaction mixture obtained by the first-stage reaction is stored before the second-stage reaction and the stored reaction mixture is subjected to the second-stage reaction; and (5) a method in which each of the first-stage reaction and the second-stage reaction is performed in a continuous manner, wherein the reaction mixture continuously withdrawn from the reactor used in the first-stage reaction is continuously transferred to a reactor different from that used in the first-stage reaction.

As described below in detail, method (1) has, an advantage that, even when a part of the $WA_4H_2$ products formed in the first-stage reaction deposits on the heterogeneous reduction catalyst, the $WA_4H_2$ products deposited on the catalyst are caused to be contained in the reaction mixture obtained by the second-stage reaction, thereby preventing the loss of the $WA_4H_2$. In the second-stage reaction, water is added to the reaction system, and hence, the composition of the reaction system of the first-stage reaction is different from that of the reaction system of the second-stage reaction. Therefore, in method (1), for performing the first-stage reaction using the reactor which has already been used in the second-stage reaction, it is necessary to wash the inside of the reactor before performing the first-stage reaction therein. On the other hand, in method (2), the first-stage reaction and the second-stage reaction are performed using different reactors. Therefore, method (2) is advantageous in that, by using two different reactors which are, respectively, used only for the first-stage reaction and only for the second-stage reaction, the operation of washing the reactor can be omitted. In the case of methods (3) to (5) (in which one or both of the first-stage reaction and the second-stage reaction is or are performed in a continuous manner), each of these methods (continuous methods) is advantageous in that, even when the first-stage reaction and/or the second-stage reaction is or are performed using a reactor(s) having a small capacity, it is possible to achieve a satisfactory production rate. However, each of these methods has a disadvantage in that the yield of the desired product tends to be lowered. Methods (1) and (2), each of which is a batchwise method (non-continuous method), do not have the above-mentioned advantage achieved by the continuous methods; however, these batchwise methods are advantageous in that the desired product can be obtained in high yield, as compared to those in the case of the continuous methods.

Hereinbelow, explanation is made with respect to the above-mentioned preferred mode (first-stage/second-stage reaction mode) of the method of the present invention, taking as examples method (1) (in which, after the first-stage reaction, in situ, the second-stage reaction is performed using the same reactor as used in the first-stage reaction) and methods in which at least one of the first-stage reaction and the second-stage reaction is performed in a continuous manner.

One feature of method (1) of the first-stage/second-stage reaction mode (i.e., a method in which, after the first-stage reaction, in situ, the second-stage reaction is performed using the same reactor as used in the first-stage reaction) resides in that the heterogeneous reduction catalyst used in the first-stage reaction is also used as the heterogeneous reduction catalyst for the second-stage reaction. This method is very advantageous, as compared to a method in which the catalyst contained in the first-stage reaction mixture is filtered off to obtain a filtrate, and then, to the obtained filtrate is added a fresh heterogeneous reduction catalyst for the second-stage reaction. That is, in this method, when an amide group-containing solvent is used as solvent (e), due to the low solubility of the $WA_2H_4$ in the amide group-containing solvent, a part of the $WA_4H_2$ products formed in the reaction system of the first-stage reaction is caused to deposit on the heterogeneous reduction catalyst depending on the reaction conditions employed. Even in this case, by method (1) in which the heterogeneous reduction catalyst used in the first-stage reaction is also used as the heterogeneous reduction catalyst for the second-stage reaction, the $WA_4H_2$ products deposited on the catalyst are caused to be contained in the reaction mixture obtained by the second-stage reaction, thereby preventing the loss of the $WA_4H_2$.

Further, another feature of method (1) of the first-stage/second-stage reaction mode resides in that, during the time period between the end of the first-stage reaction and the start of the second-stage reaction and/or during the second-stage reaction, the amount of the reducing agent in the reaction system is maintained at a level sufficient for reducing the tetraacylhexaazaisowurtzitane derivatives contained in the reaction mixture obtained by the first-stage reaction (for example, the reducing agent may be caused to be present in the reaction system in an amount which is 80% or more of the saturation concentration of the reducing agent in the reaction system under the reaction conditions (temperature and pressure) employed). The first-stage/second-stage reaction mode can be advantageously used for achieving a high production rate of the desired $WA_4H_2$. However, in the case where, during the time period between the end of the first-stage reaction and the start of the second-stage reaction and/or during the second-stage reaction, the amount of the reducing agent in the reaction system becomes insufficient for reducing the tetraacylhexaazaisowurtzitane derivatives contained in the reaction mixture obtained by the first-stage reaction, there is a danger that the lowering of the activity of the catalyst occurs. Therefore, for surely achieving the high production rate of the desired $WA_4H_2$, it is important to maintain the amount of the reducing agent in the reaction system at a level which is sufficient for reducing the tetraacylhexaazaisowurtzitane derivatives. As described in detail below, in the second-stage reaction, for rendering easy the separation of the produced $WA_4H_2$ from the reaction system, water is added to the reaction system (reaction mixture). However, the addition of water to the reaction system tends to lower the amount of the reducing agent (such as hydrogen gas) dissolved in the reaction system. Therefore, when there is a danger that the addition of water lowers the amount of the reducing agent dissolved in the reaction system to a level which is smaller than the stoichiometric amount for the second-stage reaction (reductive dearylmethylation reaction on the tetraacylhexaazaisowurtzitane derivatives), it is necessary to increase the supply of the reducing agent to the reaction system (by, for example, increasing the pressure of hydrogen as the reducing agent to a level which is higher than that in the first-stage reaction) to thereby maintain the amount of the reducing agent dissolved in the reaction solution at a satisfactory level.

Still another feature of method (1) of the first-stage/second-stage reaction mode resides in that, after the first-stage reaction, water is added to the reaction system at one or more points in time before and during the second-stage reaction (preferably, before the start of the second-stage reaction). The reason for the addition of water to the reaction system is as follows. The $WA_4H_2$ has characteristics such that it is almost insoluble in an amide-group containing solvent and other ordinary organic solvents; however, it is soluble in water. In the present invention, utilizing the above characteristics of the $WA_4H_2$, water is used to dissolve therein the $WA_4H_2$ to thereby separate the $WA_4H_2$ from the catalyst. With respect to the timing for the addition of water to the reaction system, there is no particular limitation as long as the addition is conducted after the first-stage reaction and before the separation of the heterogeneous reduction catalyst from the reaction mixture containing the $WA_4H_2$, which is described below. However, for preventing the $WA_4H_2$ from strongly adsorbing on the heterogeneous reduction catalyst, it is preferred that water is added to the reaction system before or simultaneously with the start of the second-stage reaction.

The amount of water added to the reaction system is generally in the range of from 0.01 to 100, preferably from 0.1 to 10, more preferably from 0.2 to 5, in terms of the weight ratio of the water to the solvent (e.g., an amide group-containing solvent) used in the first-stage reaction.

Examples of reducing agents used in the second-stage reaction include hydrogen gas and hydrazine. Of these, hydrogen gas is preferred.

When hydrogen gas is used as the reducing agent in the second-stage reaction, the pressure (reaction pressure) is generally in the range of from 0.01 to 200 kgf/cm$^2$, preferably from 0.1 to 100 kgf/cm$^2$, more preferably from 1 to 50 kgf/cm$^2$, more preferably from 8 to 12 kgf/cm$^2$, in terms of the partial pressure of the hydrogen gas. In the present invention, the hydrogen gas may be used in combination with an inert gas, such as nitrogen gas, argon gas or helium gas. When use is made of a reducing agent (such as hydrazine) other than hydrogen gas in the second-stage reaction, the amount of the reducing agent (other than hydrogen gas) is generally in the range of from 1 to 10,000, preferably from 1 to 2,000, in terms of the molar ratio of the reducing agent to the arylmethyl groups of the $WA_4B_2$ and the $WA_4BH$, which are present in the reaction system.

The reaction temperature in the second-stage reaction is generally in the range of from 40 to 200° C., preferably from 60 to 160° C., more preferably from 80 to 160° C., most preferably from 80 to 130° C.

After completion of the second-stage reaction, a high purity $WA_4H_2$ can be obtained as follows. First, the heterogeneous reduction catalyst (b) is separated from the second-stage reaction mixture, to thereby obtain a liquid mixture. Then, the obtained liquid mixture is subjected to the above-mentioned distillative crystal deposition, to thereby deposit a high purity $WA_4H_2$.

Therefore, in the method of the present invention, it is preferred that heterogeneous reduction catalyst (b) is separated from the reaction mixture (containing the $WA_4H_2$) obtained in the second-stage reaction of the first-stage/second-stage reaction mode, to thereby obtain a liquid mixture containing no catalyst (which contains solvent (e), the $WA_4H_2$ and water), and then, the obtained liquid mixture is subjected to distillation to remove water, thereby depositing crystals of the $WA_4H_2$ (distillative crystal deposition).

After the distillative crystal decomposition, the deposited crystals of $WA_4H_2$ can be separated by filtration in the same manner as mentioned above.

In the method of the present invention, it is most preferred to recycle the reaction solvent (e) and water used in the second-stage reaction.

After separating the heterogeneous reduction catalyst (b) by filtration and removing water from the reaction mixture by distillation, the reaction solvent (e) can be separated and recovered by subjecting the resultant liquid mixture to distillation. Hereinbelow, the separation and the recovery of the reaction solvent (e) are explained, taking as an example of the case where the amide-group containing solvent (which is preferably used in the present invention) is used as the solvent (e).

The liquid mixture obtained after the separation of the heterogeneous reduction catalyst (b) by filtration and the removal of water by distillation contains not only the amide group-containing solvent, but also a by-produced carboxylic acid derived from the acylating agent. Since the by-produced carboxylic acid causes the skeletal decomposition of the $WB_6$, when it is intended to recycle the reaction solvent (e), it is preferred to remove the by-produced carboxylic acid as much as possible. The amount of the by-produced carboxylic acid in the recycled solvent is preferably in the range of from 0.000001 to 0.1, more preferably from 0.000001 to 0.05, most preferably from 0.000001 to 0.02, in terms of the weight ratio of the carboxylic acid to the solvent.

Some of the amide-group containing solvents form maximum boiling-point azeotropic compositions with the by-produced carboxylic acid. In the case of such solvents, it is very difficult to remove the carboxylic acid from the solvents. However, it is possible to remove the carboxylic acid from such solvents by a method in which another solvent capable of forming an azeotropic mixture with the carboxylic acid at a low boiling point is added to the solvent, and the formed azeotropic mixture is distilled. There are various solvents which are capable of forming a low boiling-point azeotropic mixture with the carboxylic acid, and any of such solvents can be used in the present invention. However, it is preferred to use an arylmethane, such as toluene or xylene, which is a representative example of the solvents capable of forming a low boiling-point azeotropic mixture. Further, it is especially preferred to recycle and use the arylmethane by-produced in the reductive dearylmethylation in the first-stage reaction and/or the second-stage reaction. With respect to the timing for conducting the azeotropic distillation and to a method for conducting the azeotropic distillation, there is no particular limitation. For example, it is preferred that the azeotropic distillation is conducted by a method wherein the by-produced carboxylic acid and the arylmethane are removed by azeotropic distillation from: (x) the reaction mixture obtained by the reductive dearylmethylation/ acylation (first-stage reaction); or (y) the reaction mixture at the time of the removal of water by distillation after the second-stage reaction; and (z) a portion of the reaction mixture which portion remains after the deposited $WA_4H_2$ crystals have been isolated from the reaction mixture.

Further, when use is made of the amide group-containing solvent which forms a maximum boiling-point composition with the carboxylic acid, the removal of the by-produced carboxylic acid can also be conducted by a method in which the carboxylic acid is reacted with a basic substance, to thereby immobilize the by-produced carboxylic acid on the basic substance, and then, the immobilized carboxylic acid is removed from the solvent.

Representative examples of the method for immobilizing the carboxylic acid include: ($\alpha$) a method in which a carboxylic acid salt is formed by a neutralization reaction between a basic substance and the carboxylic acid; and ($\beta$) a method in which the carboxylic acid is immobilized by adsorption on an adsorbent, such as an amine type anion-exchange resin which is capable of adsorbing carboxylic anions thereon.

With respect to method ($\alpha$), there is no particular limitation with respect to the basic substance used for forming a carboxylic acid salt by a neutralization reaction; however, it is preferred to use a basic metal compound. With respect to the basic metal compound used in method ($\alpha$), it is preferred to use a basic metal compound containing an alkali metal or an alkaline earth metal, such as sodium, potassium, lithium, magnesium or calcium. Preferred examples of basic metal compounds include hydroxides of an alkali metal or an alkaline earth metal, such as NaOH, KOH, LiOH, $Mg(OH)_2$ and $Ca(OH)_2$; and oxides of an alkali metal or an alkaline earth metal, such as MgO and CaO. Among these basic metal compounds, basic magnesium compounds (such as $Mg(OH)_2$ and MgO) are especially preferred, because these compounds form magnesium salts of the carboxylic acid, which have high affinity to the amide group-containing solvent. With respect to the method for recovering the amide group-containing solvent after the formation of the salt of the carboxylic acid, distillation is preferred. When the solvent containing the salt of the carboxylic acid is subjected to distillation, since the salt of the carboxylic acid, which is the main component of the residue remaining in the still, has high affinity to the amide group-containing solvent (the magnesium salt of the carboxylic acid has especially high affinity to the amide-containing solvent), the residue can be withdrawn in the form of a low viscosity slurry. Such characteristics of the salt of the carboxylic acid is very advantageous because the adherence of the solid substance to the inner wall of the still, which changes the heat transfer coefficient between the heat source and the solvent to be distilled off to thereby render unstable the distillation conditions, would not occur.

Hereinbelow, explanation is made with respect to the reaction conditions for immobilizing the carboxylic acid by neutralization reaction using a basic substance.

With respect to the amount of the basic substance, the basic substance can be used in an amount such that about 80% of the carboxylic acid present in the solvent are neutralized or an amount larger than the above-mentioned amount. Alternatively, the addition of the basic substance can be conducted by a method in which the basic substance is dropwise added to the solvent while measuring the pH value of the resultant mixture, and the addition is stopped when the pH value of the mixture becomes 6.5 or more. In this instance, it is especially preferred to stop the neutralization reaction at a pH value of 7 or more (i.e., at a basic pH) in order to increase the neutralization ratio of the carboxylic acid.

With respect to the neutralization temperature, the neutralization can be conducted at 20 to 160° C.

After removing the by-produced carboxylic acid from the liquid mixture by method ($\alpha$) or ($\beta$), the resultant mixture is subjected to distillation, thereby obtaining an amide group-containing solvent which can be recycled. The obtained amide group-containing solvent contains not only the by-product carboxylic acid, but also an arylmethane by-produced during the dearylmethylation and water used in the second-stage reaction. With respect to the amide group-containing solvent recovered by distillation, it is preferred that the water content of the solvent is in the range of from 0.0001 to 0.1, more preferably 0.0001 to 0.05, most preferably 0.0001 to 0.03, and that the arylmethane content of the solvent is in the range of from 0.0000001 to 0.1, more preferably 0.0000001 to 0.05, most preferably 0.0000001 to 0.01, in terms of the weight ratio thereof to the amide group-containing solvent.

The water used in the second-stage reaction is removed from the reaction mixture in the distillative crystal deposition. The water removed from the reaction mixture in the distillative crystal deposition has low purity, but such a low purity water as such can be recycled to the second-stage reaction system, without causing any adverse effects on the reaction. However, it is preferred to treat such a low purity water by a method in which the low purity water (comprising the distilled water and the by-produced arylmethane) is separated into two phases, and then, the water (aqueous phase) is isolated.

Method (2) of the first-stage/second-stage reaction mode is a method in which, after the first-stage reaction, the reaction mixture obtained by the first-stage reaction is transferred to a reactor different from that used in the first-stage reaction, and the second-stage reaction is performed in this different reactor (in method (2), the heterogeneous reduction catalyst contained in the reaction mixture obtained by the first-stage reaction may be separated and recovered from the reaction mixture by filtration or the like, and a fresh heterogeneous reduction catalyst may be added to the resultant mixture.)

In method (2), it is preferred to prevent the occurrence of a phenomenon such that the reducing agent (such as hydrogen) escapes from the first-stage reaction mixture after the first-stage reaction so that the tetraacylhexaazaisowurtzitane derivatives of formula (3) contacts the heterogeneous reduction catalyst in the absence of the reducing agent. For this purpose, it is preferred to continuously add the reducing agent to the reaction mixture until the second-stage reaction is started. When the heterogeneous reduction catalyst contained in the first-stage reaction mixture is separated and recovered from the reaction mixture, and a fresh heterogeneous reduction catalyst is added to the reaction mixture, it is difficult to continue the addition of the reducing agent to the reaction mixture. In such a case, it is preferred that, after the addition of the reducing agent to the reaction mixture is started, a fresh catalyst is added to the reaction mixture to start the reaction.

The amount of the fresh catalyst added to the reaction mixture obtained in the first-stage reaction varies depending on the catalyst activity of the catalyst used; however, the amount of the fresh catalyst is generally within the range of from 0.0001 to 0.5, preferably from 0.001 to 0.3, more preferably from 0.01 to 0.2, in terms of the weight ratio thereof to the solvent.

After the second-stage reaction, the distillative crystal deposition can be performed in the same manner as described above in connection with method (1) to thereby obtain high purity crystals of the $WA_4H_2$.

Further, the $WA_4H_2$ can be obtained by filtration after the distillative crystal deposition in substantially the same manner as described above in connection with method (1).

In addition, it is most preferred to recycle the reaction solvent (e) and water used in the second-stage reaction in substantially the same manner as described above in connection with method (1).

Method (3) of the first-stage/second-stage reaction mode (that is, a method in which the first-stage reaction or the second-stage reaction is performed in a continuous manner) is a method in which the reductive dearylmethylation/acylation reaction of the $WB_6$ is conducted in a continuous manner using a complete mixing type reactor.

First, explanation is made with respect to the case where the first-stage reaction is performed in a continuous manner.

When the first-stage reaction is conducted in a continuous manner, it is preferred that the residence time of the reaction mixture in the reactor is within 10 hours.

Further, it is preferred that the continuous reaction using a complete mixing type reactor is performed at a high rate such that the total weight of the $WB_6$, the $WAB_5$, the $WA_2B_4$ and the $WA_3B_3$, which are present in the reaction system, becomes 10% by weight or less, based on the total weight of the hexaazaisowurtzitane derivatives present in the reaction system.

The reaction rate can be controlled by changing the amount of the reducing agent, the reaction temperature, and the activity and amount of the catalyst employed. It is especially effective to control the reaction rate by changing the amount of the catalyst employed. The desirable amount of the catalyst is influenced by the activity of the catalyst. However, generally, the above-mentioned high reaction rate can be achieved by using the catalyst in an amount of from 0.01 to 0.4, preferably 0.02 to 0.2, in terms of the weight ratio thereof to the solvent.

The reaction rate is also greatly influenced by the weight ratio of the catalyst (b) to the $WB_6$ (a). For example, in the case where the catalyst (b) is first charged into the reactor, and then, a reaction is performed by continuously charging the $WB_6$ into the reactor, the above-mentioned high reaction rate can be achieved by charging $WB_6$ in an amount of from 0.00001 to 0.5, preferably from 0.00005 to 0.1, more preferably from 0.0001 to 0.01, in terms of the ratio of the charging rate ($K_1$ (g/min)) of the $WB_6$ (a) to the amount ($Q_1$ (g)) of the catalyst present in the reactor.

When the first-stage reaction is performed in a continuous manner, it is preferred that the amount of the by-produced carboxylic acid (derived from the acylating agent) present in the reaction system is 0.1 or less, in terms of the weight ratio thereof to the solvent present in the reaction system. For reducing the amount of the by-produced carboxylic acid present in the reaction system to less than 0.1, in terms of the weight ratio thereof to the solvent present in the reaction system, the $WB_6$ is used in an amount such that the concentration of the $WB_6$ in the reaction system becomes 0.0001 to 0.2, preferably 0.001 to 0.15, more preferably 0.01 to 0.1, in terms of the weight ratio of the $WB_6$ to the solvent present in the reaction system.

In method (3), when the reaction is performed while confining the heterogeneous catalyst (b) inside the reactor, it is preferred that the $WA_4B_nH_{(2-n)}$ (n is 1 or 2) is dissolved in the solvent (e). The solubility of the $WA_4B_nH_{(2-n)}$ (n is 1 or 2) in the reaction solvent is influenced by the type of the reaction solvent used and the reaction temperature; however, for obtaining a reaction mixture wherein the $WA_4B_nH_{(2-n)}$ (n is 1 or 2) is dissolved in the reaction solvent (e), the reaction is preferably conducted under conditions such that the weight ratio of the $WA_4B_nH_{(2-n)}$ (n is 1 or 2) in the reaction mixture to the reaction solvent (e) becomes 0.001 to 0.2, more preferably 0.01 to 0.1, most preferably 0.02 to 0.07.

The $WA_4B_nH_{(2-n)}$ (n is 1 or 2) is relatively stable when the compound is present in an amide group-containing solvent in the state of supersaturation. Therefore, even when a large amount of the $WA_4B_nH_{(2-n)}$ (n is 1 or 2) is formed in the amide group-containing solvent, the deposition of the compound would not easily occur and the compound remains to be dissolved in the solvent for a relatively long period of time. Therefore, by using a short residence time, it is possible to continuously withdraw a reaction mixture in which the $WA_4B_nH_{(2-n)}$ (n is 1 or 2) is present in the state of supersaturation, without the deposition of the compound on the catalyst confined in the reactor.

Further, in the first-stage reaction, a small amount of the $WA_4H_2$ is also formed by the further reductive dearylmethylation of the $WA_4B_nH_{(2-n)}$ (n is 1 or 2). As in the case of the $WA_4B_nH_{(2-n)}$ (n is 1 or 2), the $WA_4H_2$ is also relatively stable in an amide group-containing solvent in the state of supersaturation. Therefore, by the use of a short residence time, it is possible to withdraw a reaction mixture in which the $WA_4H_2$ is present in the state of supersaturation, without the deposition of the compound on the heterogeneous reduction catalyst confined in the reactor.

Alternatively, in performing the continuous reaction, the heterogeneous reduction catalyst (b) may be flowed through the reactor, instead of confining the catalyst in the reactor. Specifically, for example, the continuous reaction can be performed by a method in which a solution (obtained by dissolving the $WB_6$ (a) in the amide group-containing organic solvent (e)), the acylating agent (c), the heterogeneous reduction catalyst (b) (which may be in the form of a slurry obtained by dispersing the catalyst (b) in the amide group-containing solvent (e)), and the reducing agent (d) are charged into a reactor under such conditions as defined in the present invention, and a reaction mixture containing the heterogeneous reduction catalyst is withdrawn from the reactor in the form of a slurry. In this method, even when the $WA_4H_2$ having low solubility in the amide group-containing organic solvent (e) is formed in a large amount in the first-stage reaction, the reaction mixture (containing both of the catalyst and the $WA_4H_2$) obtained in the first-stage reaction is subjected to the second-stage reaction wherein water as a good solvent for the $WA_4H_2$ is added to the reaction mixture, followed by the separation of the catalyst from the reaction mixture.

With respect to the reactor for conducting the first-stage reaction in a continuous manner, it is preferred to use a multi-stage reaction vessel generally employed in the art for performing a continuous reaction. There is no particular limitation with respect to the number of stages as long as the number of stages is 2 or more. However, the larger the number of stages, the more advantageous.

Further, in the present invention, the first-stage reaction can be performed intermittently by repeating a sequence of: the first-stage reaction in a reactor for a predetermined period of time; the withdrawal of a predetermined amount of the reaction mixture obtained by the first-stage reaction from the reactor; and the introduction of the raw material liquid into the reactor in an amount corresponding to the above-mentioned predetermined amount. When the reaction is conducted in such a manner, the amount of reaction mixture withdrawn at a time is preferably within the range of from 1/1000 to all of the reaction mixture in the reactor.

When the $WB_6$ is intermittently charged into the reactor, the amount ($Q'_1$ (g)) of the catalyst in the reactor, the amount ($p_1$ (g)) of the $WB_6$ charged into the reactor at a time, the interval ($t_1$ (min)) between the charges of the $WB_6$ to the reactor are selected so that the value of $(p_1/t_1)/Q'_1$ is generally within the range of from 0.00001 to 0.5, preferably from 0.00005 to 0.1, more preferably from 0.0001 to 0.01.

In method (3), the first-stage reaction can be performed in a continuous manner in substantially the same manner as mentioned above in connection with the first-stage reaction of method (1), except for the special conditions mentioned above.

Next, explanation is made with respect to the case where the second-stage reaction is performed in a continuous manner.

When the second-stage reaction is conducted in a continuous manner, it is preferred that the $WA_4B_nH_{(2-n)}$ is dissolved in the solvent (e). The solubility of the $WA_4B_nH_{(2-n)}$ in the reaction solvent is influenced by the type of the reaction solvent used and the reaction temperature; however, for obtaining a reaction mixture wherein the $WA_4B_nH_{(2-n)}$ (n is 1 or 2) is dissolved in the reaction solvent (e), the reaction is preferably performed under conditions such that the weight ratio of the $WA_4B_nH_{(2-n)}$ in the reaction mixture to the reaction solvent (e) becomes 0.001 to 0.1, preferably 0.005 to 0.07, more preferably 0.007 to 0.05.

The $WA_4B_nH_{(2-n)}$ is relatively stable in the reaction solvent in the state of supersaturation. Therefore, even when a large amount of the $WA_4B_nH_{(2-n)}$ (n is 1 or 2) is formed in the amide group-containing solvent, the deposition of the compound would not easily occur and the compound remains dissolved in the solvent for a relatively long period of time. Therefore, by using a short residence time, it is possible to continuously withdraw a reaction mixture in which the $WA_4B_nH_{(2-n)}$ (n is 1 or 2) is present in the state of supersaturation.

With respect to the reducing agent and the reduction catalyst which can be used for performing the second-stage reaction in a continuous manner, use can be made of the same reducing agent and the same reduction catalyst as used in the first-stage reaction.

In the second-stage reaction, the catalyst used in the first-stage reaction as such can be employed; however, if desired, the second-stage reaction can be performed while adding a fresh catalyst to the second-stage reaction system. The desirable amount of the catalyst present in the reaction system varies depending on the catalytic activity of the catalyst. However, the fresh catalyst is added to the reaction system in an amount such that the weight ratio of the catalyst in the reaction system to the solvent becomes 0.0001 to 0.5, preferably 0.001 to 0.3, more preferably 0.01 to 0.2.

With respect to the reactor for conducting the second-stage reaction in a continuous manner, it is preferred to use a multi-stage reaction vessel generally employed in the art for performing a continuous reaction. There is no particular limitation with respect to the number of stages as long as the number of stages is 2 or more. However, the larger the number of stages, the more advantageous.

Further, in the present invention, the second-stage reaction can be conducted intermittently by repeating a sequence of: the second-stage reaction for a predetermined period of time; the withdrawal of a predetermined amount of the reaction mixture obtained by the second-stage reaction from the reactor; and the introduction of the first-stage reaction mixture into the reactor in an amount corresponding to the above-mentioned predetermined amount. When the reaction is conducted in such a manner, the amount of reaction mixture withdrawn at a time is preferably within the range of from 1/1000 to all of the reaction mixture in the reactor.

After the second-stage reaction, the distillative crystal deposition can be performed in substantially the same manner as described above in connection with method (1) to thereby obtain high purity crystals of the $WA_4H_2$.

Further, the $WA_4H_2$ can be obtained by filtration after the distillative crystal deposition in substantially the same manner as described above in connection with method (1).

In addition, it is most preferred to recycle the reaction solvent (e) and water used in the second-stage reaction in substantially the same manner as described above in connection with method (1).

Method (4) of the first-stage/second-stage reaction mode (that is, a method in which each of the first-stage reaction and the second stage reaction is performed in a continuous manner, wherein the reaction mixture obtained by the first-stage reaction is stored before the second-stage reaction and the stored reaction mixture is subjected to the second-stage reaction) is a method in which each of the first-stage reaction and the second stage reaction is performed in a continuous manner as described above in connection with method (3), wherein the reaction mixture obtained by the first-stage reaction is stored before the second-stage reaction and the stored reaction mixture is subjected to the second-stage reaction. This method is advantageous in that the desired $WA_4H_2$ can be efficiently produced.

After the second-stage reaction, the distillative crystal deposition can be performed in the same manner as described above in connection with method (1) to thereby obtain high purity crystals of the $WA_4H_2$.

Further, the $WA_4H_2$ can be obtained by filtration after the distillative crystal deposition in substantially the same manner as described above in connection with method (1).

In addition, it is most preferred to recycle the reaction solvent (e) and water used in the second-stage reaction in substantially the same manner as described above in connection with method (1).

Method (5) of the first-stage/second-stage reaction mode (that is, a method in which each of the first-stage reaction and the second-stage reaction is performed in a continuous manner, wherein the reaction mixture continuously withdrawn from a reactor used in the first-stage reaction is continuously transferred to a reactor different from that used in the first-stage reaction) is a method in which each of the first-stage reaction and the second stage reaction is performed in a continuous manner as described above in connection with method (3), wherein the reaction mixture continuously withdrawn from a reactor used in the first-stage reaction is continuously transferred to a reactor different from that used in the first-stage reaction. This method is advantageous in that the desired $WA_4H_2$ can be obtained very efficiently, even as compared to method (4).

After the second-stage reaction, the distillative crystal deposition can be performed in substantially the same manner as described above in connection with method (1) to thereby obtain high purity crystals of the $WA_4H_2$.

Further, the $WA_4H_2$ can be obtained by filtration after the distillative crystal deposition in substantially the same manner as described above in connection with method (1).

In addition, it is most preferred to recycle and reuse the reaction solvent (e) and water used in the second-stage reaction in substantially the same manner as described above in connection with method (1).

In the method of the present invention, it is preferred to use a $WB_6$ having a purity of 95% or more. The use of such a high purity $WB_6$ is advantageous not only in that the rate of reductive dearylmethylation/acylation of hexakis(arylmethyl)hexaazaisowurtzitane (i.e., $WB_6$) can be increased, but also in that the desired tetraacylhexaazaisowurtzitane derivatives can be obtained in high yield.

The $WB_6$ can be synthesized by dehydration condensation reaction of glyoxal and an arylmethylamine. The reaction is performed in a solvent in the presence of a catalyst, and the formed $WB_6$ is deposited as crystals in the resultant reaction mixture. The purity of the $WB_6$ has a great influence on the rate of the reductive dearylmethylation/acylation reaction. Therefore, a method for stably producing a high purity $WB_6$ is a very important technique for the commercial-scale production of tetraacylhexaazaisowurtzitane derivatives. Explanation is made below with respect to the method for obtaining a high purity $WB_6$, specifically, the method for the synthesis and crystallization of the $WB_6$.

The high purity $WB_6$ crystals can be produced by using an arylmethylamine and glyoxal (that is, the raw materials) in amounts such that the molar ratio of the arylmethylamine to glyoxal becomes 3 or more. The molar ratio of arylmethylamine to glyoxal is preferably in the range of from 3 to 100, more preferably from 4 to 10.

The reaction conditions for synthesizing the $WB_6$ are explained hereinbelow.

With respect to a solvent used for synthesizing $WB_6$, a solvent having high polarity can be used. Examples of high polarity solvents include nitrites, amides, amines, alcohols and water. These solvents can be used individually or in combination. It is preferred to use at least one solvent selected from the group consisting of alcohols, nitriles and water. Specifically, it is preferred to use at least one solvent selected from the group consisting of nitrites, such as acetonitrile, propionitrile and butyronitrile; amides, such as N,N-dimethylacetamide, N,N-dimethylformamide and N-methyl-2-pyrrolidone; amines, such as benzylamine; alcohols, such as methanol, ethanol, propanol and butanol; and water. More preferred is a mixed solvent of acetonitrile and water. Further, the use of a solvent having a low ability to dissolve the $WB_6$ is advantageous in that the crystal deposition yield of the synthesized $WB_6$ becomes high.

Examples of catalysts used for synthesizing $WB_6$ include Brønsted acids, ammonium salts, alkylamine salts, polymeric acidic solids and salts thereof. Examples of Brønsted acids include carboxylic acids, such as formic acid, acetic acid, propionic acid and benzoic acid; and mineral acids, such as sulfuric acid and nitric acid. Among these, preferred are formic acid, acetic acid and propionic acid. Examples of salts include ammonium salts, such as ammonium formate, ammonium acetate and ammonium propionate; alkylamine salts, such as benzylamine hydrochloride, benzylamine sulfate, ethylamine hydrochloride, propylamine hydrochloride, triethylamine hydrochloride, benzylamine propionate, benzylamine acetate, benzylamine formate, aniline acetate, aniline formate, ethylamine acetate, propylamine acetate, butylamine acetate, diethylamine acetate and triethylamine acetate; and arylamine salt.

As a polymeric acidic solid and a salt thereof, use can be made of an acid-type or a neutral salt-type cation exchange resin and a neutral salt-type anion exchange resin. Preferably, an acid-type weakly acidic ion exchange resin, a neutral salt-type weakly acidic ion exchange resin, and a neutral salt-type weakly basic ion exchange resin are used.

The concentration of the catalyst is in the range of from 0.001 to 10, preferably from 0.1 to 5, in terms of the molar ratio of the catalyst to glyoxal. When an ion exchange resin is used as a catalyst, the concentration of the catalyst is in the range of from 0.1 to 1000, preferably from 0.1 to 20, in terms of the weight ratio of the catalyst to glyoxal.

There is no particular limitation with respect to the temperature for synthesizing $WB_6$ as long as the temperature is in the range of from the freezing point of the solvent to the boiling point of the solvent, but preferably, the temperature is of from −10 to 60° C.

With respect to the glyoxal used for synthesizing WB$_6$, either an aqueous solution of glyoxal or 100% glyoxal can be used. In the case of an aqueous solution of glyoxal, use is made of an aqueous solution of glyoxal having a concentration of 10% by weight or more, relative to the total weight of the aqueous solution. The glyoxal concentration of the glyoxal solution is preferably in the range of from 10 to 90% by weight, more preferably from 20 to 60% by weight. Further, when glyoxal is used in the form of an aqueous solution, the purity of glyoxal with respect to the part excluding water is generally in the range of 80% or more, preferably 90% or more, and more preferably 95% or more.

The concentration of glyoxal in the reaction solution for synthesizing WB$_6$ is in the range of from 0.001 to 0.5, preferably from 0.005 to 0.4, more preferably from 0.005 to.0.2, in terms of the weight ratio of glyoxal to the solution.

The synthesis of WB$_6$ comprises the following steps (I) to (III):

(I) adding glyoxal to a solution obtained by mixing an arylmethylamine, a catalyst and a solvent, wherein the molar ratio of the arylmethylamine to glyoxal is appropriately selected so as to be 3 or more to thereby generate WB$_6$, which is spontaneously crystallized, to thereby obtain crystals of WB$_6$;

(II) separating the crystals of WB$_6$ deposited from the reaction mixture; and (III) washing the crystals of WB$_6$ with a solvent containing an organic solvent.

The addition of glyoxal in the above-mentioned process (I) may be conducted over a period of time of from 5 minutes to 10 hours.

With respect to the method for separating the crystals of WB$_6$ in the above-mentioned step (II), a general method for the separation of a solid phase from liquid phase can be employed. Examples of such methods include suction filtration and pressure filtration using a membrane filter, and centrifugation.

With respect to the solvent for washing the crystals of WB$_6$ in the above-mentioned process (III), there is no particular limitation as long as the solubility of WB$_6$ in the solvent is 10 g/l or less and the solvent does not react with WB$_6$. Specifically, the same solvent as used for the synthesis and crystallization of WB$_6$ can be employed. The solubility of WB$_6$ in such a solvent is sometimes more than 10 g/l at room temperature. However, in that case, the solubility of WB$_6$ in such a solvent can be lowered to 10 g/l or less by conducting the washing at a temperature of about −20° C. Examples of solvents, in which the solubility of WB$_6$ in the solvent is 10 g/l or less at room temperature, include nitriles, such as acetonitrile, propionitrile and butyronitrile; alcohols, such as methanol, ethanol, propanol, butanol, pentanol, hexanol, heptanol and octanol. Further, it is more preferred to use a mixed solvent of the above-mentioned nitrile and/or alcohol and water as a solvent for washing the crystals of WB$_6$, because of the excellent washing effect of such a mixed solvent and the low solubility of WB$_6$ in such a mixed solvent. When such a mixed solvent is used as a solvent for washing the crystals of WB$_6$, the content of water in the mixed solvent may generally be 30% by weight or less, preferably from 5 to 20% by weight, based on the total weight of the mixed solvent. It is most preferable to use a mixed solvent of acetonitrile and water as a solvent for washing the crystals of WB$_6$, wherein the content of water in the mixed solvent is from 5 to 20% by weight, based on the total weight of the mixed solvent.

The above-mentioned method using an excess amount of an arylmethylamine (i.e., the molar ratio of the arylmethylamine to glyoxal is 3 or more) makes it possible to produce WB$_6$ having a purity as high as 95% or more.

When a method other than the above-mentioned method is employed for producing WB$_6$, the purity of the final WB$_6$ is disadvantageously low. In other words, when a method for producing WB$_6$, wherein the method is substantially the same as the above-mentioned method, except that the molar ratio of the arylmethylamine to glyoxal is less than 3, is conducted, the purity of the final WB$_6$ is disadvantageously low. However, the impurities contained in low purity WB$_6$ can be removed by an appropriate purification method using an organic solvent, to thereby obtain WB$_6$ having a high purity.

One of the conventional method for purifying WB$_6$ is described in Journal of Organic Chemistry, Vol. 55, 1459–1466 (1990). According to the method of this document, crude WB$_6$ (hexabenzylhexaazaisowurtzitane) is suspended in cold acetonitrile, and then subjected to filtration to collect WB$_6$, followed by washing. Further, the washed WB$_6$ is recrystallized from acetonitrile. However, no description with respect to the concentration of WB$_6$ relative to the solvent and the crystallization temperature is found in the above document. That is, in the above document, the conditions for removing the impurities contained in low purity WB$_6$ are not specified.

The present inventors have conducted recrystallization of WB$_6$ several times according to the method of the above document. That is, 16.68 g of crude WB$_6$ was subjected to recrystallization using 1 liter of acetonitrile to thereby obtain crystals of WB$_6$, and this recrystallization was repeated several times. The purities of the obtained crystals were determined, and it was confirmed that the purity of WB$_6$ obtained by the method of the above document varies in the range of from 85 to 100%.

Further, each batch of the crystals of WB$_6$ obtained by the method of the above document was individually subjected to dearylmethylation reaction in the presence of an acylating agent (using a palladium catalyst) to obtain acyl group-containing hexaazaisowurtzitane derivatives. As a result, it was found that the reaction time required for the dearylmethylation reaction drastically varies depending on the batch of the crystals of WB$_6$, and when a long reaction time is required for the dearylmethylation reaction, the yields of the desired acyl group-containing hexaazaisowurtzitane derivatives are extremely lowered, due to the decomposition of hexaazaisowurtzitane skeleton of WB$_6$.

In this situation, the present inventors have conducted extensive and intensive studies with a view toward developing an improved method for recrystallizing WB$_6$ in which a high purity WB$_6$ can be surely prepared from a crude WB$_6$. As a result, it has been found that the above object can be attained by the following method (hereinafter, frequently referred to as "high-purity recrystallization method"). The high-purity recrystallization method is a method for recrystallizing WB$_6$, which comprises:

dissolving crude WB$_6$ into an organic solvent, to thereby obtain a solution; and depositing crystals of highly-purified WB$_6$, wherein the type and amount of the organic solvent are selected so that by-products contained in the crude WB$_6$ are completely dissolved in the organic solvent at the temperature for depositing crystals of highly-purified WB$_6$, the by-products being detectable by high performance liquid chromatography.

Deposition of crystals of WB$_6$ can be conducted by a conventional recrystallization method. As an example of a recrystallization method, there can be mentioned a method based on the difference of the solubility of $WB_6$ depending on the difference of the temperature of the solvent used for the recrystallization, which comprises:

mixing a crude $WB_6$ with an appropriate solvent;

heating the resultant mixture to a temperature equal to or lower than the boiling point of the solvent to thereby completely dissolve the crude $WB_6$ in the solvent; and cooling the resultant solution to an appropriate temperature to thereby deposit crystals of high purity $WB_6$.

As another example of a recrystallization method, there can be mentioned a method based on the difference between the solubility of $WB_6$ in a good solvent for $WB_6$ and the solubility of $WB_6$ in a poor solvent for $WB_6$, which comprises:

dissolving a crude $WB_6$ in a good solvent for $WB_6$ at an appropriate temperature; and adding portionwise a poor solvent for $WB_6$ to the resultant solution of $WB_6$ in a good solvent for $WB_6$, to thereby deposit crystals of high purity $WB_6$.

When heating a recrystallization system is effected for dissolving $WB_6$, it is preferred that in order to avoid the lowering of the yield of the desired compound due to the thermal decomposition of $WB_6$, heating to 130° C. or less is preferred.

The deposition of crystals of high purity $WB_6$ from the recrystallization system containing $WB_6$ is generally completed in one hour to several days, wherein the recrystallization system containing $WB_6$ may be stirred or allowed to stand still. When the deposition of crystals is conducted by allowing the recrystallization system to stand still, a high purity $WB_6$ tends to be obtained in the form of relatively large needle-like crystals. On the other hand, when the deposition of crystals is conducted by stirring the recrystallization system, a high purity $WB_6$ tends to be obtained in the form of relatively fine crystals. The reproducibilities of the yield and purity of the crystals of high purity $WB_6$ can be improved by maintaining the temperature of the recrystallization system containing $WB_6$ at an appropriate temperature during the deposition of crystals.

In the above-mentioned high-purity recrystallization method, use is made of a solvent system comprising at least one type of organic solvent, wherein the solvent has a solubility ratio P of from 0.1 to 20, wherein the solubility ratio P is represented by the following formula (5):

$$P=H/I \qquad (5)$$

wherein H represents the solubility (g/l) of $WB_6$ in an organic solvent, and I represents the solubility (g/l) of the impurities (detected by high performance liquid chromatography analysis) in the organic solvent.

Hereinbelow a brief description is made on the solubility of $WB_6$ and the solubility of impurities detectable by liquid chromatography.

The solubility of $WB_6$ was calculated, based on the results of an analysis by liquid chromatography of the amount of the $WB_6$ which is dissolved in the solvent. On the other hand, the solubility of the impurities mentioned above was calculated, based on the results of an analysis by liquid chromatography of the amount of the impurities dissolved in the solution, assuming that the amount of impurities detectable by liquid chromatography is all of the remainder obtained by subtracting the amount of $WB_6$ from the amount of the crude $WB_6$.

Examples of organic solvents used for the high-purity recrystallization method include aromatic hydrocarbons, such as toluene and benzene; ethers, such as tetrahydrofuran, diethyl ether, dipropyl ether and dibutyl ether; nitriles, such as acetonitriles, propionitrile and butyronitrile; amides, such as N,N-dimethylacetamide, N,N-dimethylformamide, 1,3-dimethyl-2-imidazolidone, N-methyl-2-pyrrolidone and N,N-diethyl nipecotamide; alcohols, such as methanol, ethanol, propanol, butanol, pentanol, hexanol, heptanol and octanol; esters, such as ethyl formate, ethyl acetate, methyl acetate, propyl acetate, butyl acetate, methyl propionate, ethyl propionate, propyl propionate and butyl propionate; hydrocarbon halogenides, such as dichloromethane, chloroform and 1,2-dichloroethane. These solvents can be used individually or in combination.

In the high-purity recrystallization method, it is preferred to use an organic solvent having a small value of solubility ratio P which is represented by the above-mentioned formula (5). Preferred examples of solvents include alcohols, nitriles, esters and amides. These solvents can be used individually or in combination. More preferred are a combination of ethanol and ethyl acetate, a combination of ethanol and N,N-dimethylacetamide, and a combination of acetonitrile and N,N-dimethylacetamide. Most preferred is a mixed solvent of ethanol and ethyl acetate.

It is preferred that the organic solvent used in the high-purity recrystallization method has a temperature within the range of from 5 to 60° C., at which it exhibits an impurity dissolution of 0.90 g/l or more, in terms of the solubility of the impurities of crude $WB_6$. When such an organic solvent is used, it is possible to decrease the amount of the solvent. Further, for increasing the high-purity recrystallization yield, it is preferred to use a solvent which has a high dissolving ability for impurities and a low dissolving ability for $WB_6$. Specifically, it is preferred that the solvent has a temperature within the range of from 5 to 60° C., at which the above-mentioned P value is less than 3.8. Therefore, it is more preferred that the solvent has a temperature within the range of from 5 to 60° C., at which it exhibits an impurity dissolution of 0.90 g/l or more (with respect to the impurities of crude $WB_6$) and a $WB_6$ dissolution of less than 3.42 g/l.

In the high-purity recrystallization method, the amount of the solvent used is not particularly limited as long as the amount of the solvent is sufficient to dissolve all impurities of crude $WB_6$ at the recrystallization temperature. For example, in the case of high-purity recrystallization with respect to 100 g of crude $WB_6$ which contains 10 weight % of impurities, when the solvent used exhibits an impurity dissolution of 1 g/l at room temperature, the solvent is used in an amount of 10 liters or more. The amount of the solvent used for the high-purity recrystallization method is generally of from 10 to 10,000, preferably 20 to 200, in terms of the weight ratio of the solvent to crude $WB_6$.

Hereinbelow, explanation is made with respect to the structures of the above-mentioned compounds $WB_6$, $WA_4B_2$ and $WA_4H_2$.

The arylmethyl group represented by B in each of the formulae (1) and (3) means an aryl group (Ar)-substituted methyl group which generally has 7 to 21 carbon atoms. As a representative example of aryl-methyl groups B, there can be mentioned a group having a structure represented by the following formula (6):

$$—CH_2Ar \qquad (6)$$

wherein Ar represents an aromatic group having 6 to 20 carbon atoms.

As mentioned above, the number of carbon atoms of Ar in the formula (6) above is generally in the range of from 6 to 20, preferably from 6 to 10, most preferably 6. Examples of Ar's include a phenyl group; alkylphenyl groups, such as a tolyl group (o-, m- and p-isomers), an ethylphenyl group (o-, m- and p-isomers), and a xylyl group; alkoxyphenyl groups, such as a methoxyphenyl group (o-, m- and p-isomers), an ethoxyphenyl group (o-, m- and p-isomers), and a butoxyphenyl group (o-, m- and p-isomers); and unsubstituted and substituted naphthyl groups. Of these, preferred are a phenyl group and alkoxyphenyl groups. In the $WB_6$, the six arylmethyl groups may be the same or different.

With respect to the acyl group (A) in the formulae (3) and (4), it is preferred that the acyl group has 1 to 10 carbon atoms. Examples of acyl groups include a formyl group, an acetyl group, a propionyl group, a butyryl group, an isobutyryl group, a valeryl group, a hexanoyl group and a 2-phenylacetyl group. Of these acyl groups, acyl groups having 1 to 3 carbon atoms, such as a formyl group, an acetyl group and a propionyl group, are preferred. More preferred is an acetyl group.

With respect to the hexaazaisowurtzitane derivative represented by the formula $WA_4B_2$, it can assume a plurality of stereoisomeric configurations which are different in the positions of the acyl groups and the arylmethyl groups. The hexaazaisowurtzitane derivative represented by $WA_4B_2$ which is produced by the synthesis process used in the present invention may be any of the stereoisomers. It may be an isomer having a stereostructure represented by the following formulae (7-1) to (7-6) or optical isomers thereof.

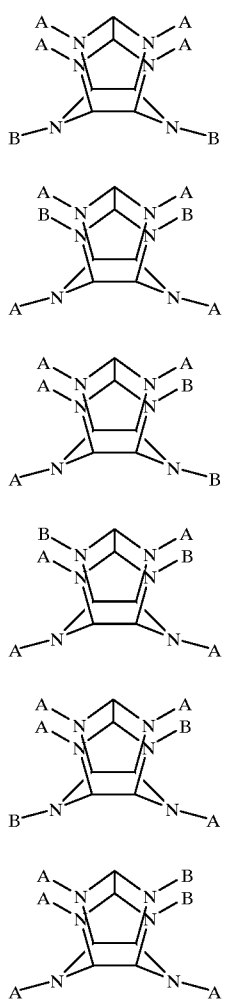

wherein A is the above-mentioned acyl group, and B is the above-mentioned arylmethyl group.

Of these compounds, most preferred is the compound of the formula (7-1).

Further, $WA_4H_2$ can assume a plurality of stereoisomeric configurations which are different in the positions of the acyl groups and the hydrogen atoms. The hexaazaisowurtzitane derivative represented by $WA_4H_2$, which is produced by the method of the present invention, may be any of the stereoisomers. Specifically, these stereoisomers are hexaazaisowurtzitane derivatives represented by the formulae (7-1) to (7-6) above wherein each of the arylmethyl groups is replaced by a hydrogen atom. Of these, most preferred is the hexaazaisowurtzitane derivative represented by the formula (7-1) above.

The reductive arylmethylation/acylation reaction in the method of the present invention is described below.

This reaction comprises the steps of: 1) subjecting $WB_6$ to reductive dearylmethylation in the presence of an acylating agent so as to convert the N-arylmethyl group contained therein to an N-H group; and 2) subsequently subjecting the resultant to acylation so as to convert the N-H group to an N-acyl group. In addition, since an N-alkyl group may be formed by the reduction (as a side reaction) of an N-acyl group, which reduction may occur depending on the reaction conditions, an N-alkyl group-containing hexaazaisowurtzitane derivative as a by-product is formed. The reaction routes have been presumed from the reaction products, and the presumed routes are shown in the chart of the following formula (8):

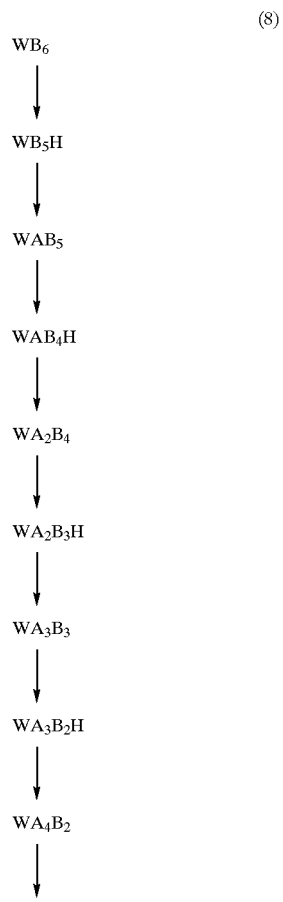

-continued

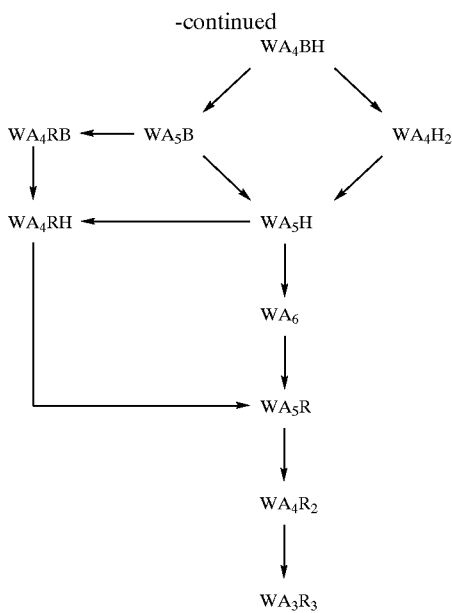

wherein A independently represents an acyl group having 1 to 10 carbon atoms, B represents an arylmethyl group having 7 to 21 carbon atoms, R independently represents an alkyl group having 1 to 10 carbon atoms, H represents a hydrogen atom, and W represents a hexavalent hexaazaisowurtzitane represented by the formula (2).

Therefore, any of the compounds shown in the chart of the formula (8) above may be contained in the reaction mixture obtained by the method of the present invention.

The method of the present invention is commercially advantageous in that tetraacylhexaazaisowurtzitane derivatives can be stably obtained in high yield. Further, in the method of the present invention, a lowering of the catalytic activity of the reduction catalyst during the reaction can be effectively suppressed to a very low level.

BEST MODE FOR CARRYING OUT THE INVENTION

Hereinbelow, the present invention will be described in more detail with reference to the following Reference Examples, Examples and Comparative Examples, which should not be construed as limiting the scope of the present invention.

(1) The abbreviations used in the following Reference Examples, Examples and Comparative Examples represent the following compounds and apparatus for analysis.

$WB_6$: hexabenzylhexaazaisowurtzitane
$WA_4B_2$: tetraacetyldibenzylhexaazaisowurtzitane
$WA_4BH$: tetraacetylbenzylhexaazaisowurtzitane
$WA_4H_2$: tetraacetylhexaazaisowurtzitane
$WA_3B_3$: triacetyltribenzylhexaazaisowurtzitane
$WA_2B_4$: diacetyltetrabenzylhexaazaisowurtzitane
DMAc: N,N-dimethylacetamide (as an organic solvent)
$Ac_2O$: acetic anhydride (as an acylating agent)
Pd—C: palladium-carbon (as a heterogeneous reduction catalyst)
HPLC: high performance liquid chromatography
GC: gas chromatography (2) The purity of $WB_6$ used in each of the following Examples and Comparative Examples is 100% unless otherwise specified.

(3) In the Examples and Comparative Examples, quantitative analyses of various hexaazaisowurtzitane derivatives were conducted in accordance with the following methods.

(i) The quantitative analysis of $WA_4H_2$ was conducted by HPLC under the following conditions using the below-described apparatus.

Conditions for HPLC Analysis

HPLC apparatus: CLASS-LC-10 System (manufactured and sold by Shimadzu Corporation, Japan)
Pump: LC10AD
Detector: SPD-10A
Controller: CLASS-LC10
Column: TSK-GEL AMIDE-80 (manufactured and sold by TOSOH, Japan)
Size: 4.6 mm×25 cm
Column temperature: 40° C.
Mobile phase: tetrahydrofuran/$H_2O$ (90/10)(v/v)
Flow rate: 1 ml/min
Detection: UV (220 nm)
The amount of a sample per injection: 5 μl Preparation of a Sample The sample for HPLC was prepared as follows unless otherwise specified.

To 0.5 ml of a reaction mixture (containing a heterogeneous reduction catalyst) obtained by the dearylmethylation in the presence or absence of an acylating agent, or a filtrate (containing no catalyst) obtained by subjecting the reaction mixture to filtration was added 30.8 ml of water, and then, the resultant mixture was subjected to ultrasonication for 5 minutes by means of an ultrasonic cleaner, and then subjected to filtration, to thereby obtain a filtrate. The obtained filtrate was used as a sample for HPLC analysis.

(ii) The quantitative analyses of $WA_2B_4$, $WA_3B_3$, $WA_4B_2$ and $WA_4BH$ were conducted by GC under the following conditions using the below-described apparatus.

Conditions for GC Analysis

GC apparatus: GC-14B type gas chromatography (manufactured and sold by Shimadzu Corporation, Japan)
Column: Metallic capillary column, Ultra ALLOY (HT) (manufactured and sold by Frontier Lab, Japan)
Inner diameter: 0.25 mm
Length: 15 m
Thickness of film coated on the inner wall of the capillary column: 0.15 μm
Detection: flame ionization detector (FID)
Temperature:
Column: 200 to 340° C. (temperature elevation rate: 15° C./min)
→340° C. (10 min)
Inlet: 340° C.
Detector: 340° C.
Carrier gas: $N_2$ (flow rate: 100 ml/min; and column internal pressure: 100 kPa)
The amount of a sample per injection: 5 μl Preparation of a Sample To 0.5 ml of a reaction mixture (containing a heterogeneous reduction catalyst) obtained by dearylmethylation in the presence or absence of an acylating agent, or a filtrate (containing no catalyst) obtained by subjecting the reaction mixture to filtration was added 23.5 ml of chloroform, and then, the resultant mixture was subjected to ultrasonication for 5 minutes by means of an ultrasonic cleaner, and then subjected to filtration, to thereby obtain a filtrate. To 4 ml of the obtained filtrate was added 0.5 ml of chloroform solution of tricosane (as an internal standard) (which was obtained by dissolving 0.4 g of tricosane in 100 ml of chloroform), to thereby obtain a solution. The obtained solution was used as a sample for GC analysis.

(iii) The quantitative analysis of $WB_6$ was conducted by HPLC under the following conditions using the below-described apparatus.

Conditions for HPLC Analysis

HPLC apparatus: CLASS-LC-10 System (manufactured and sold by Shimadzu Corporation, Japan)
Pump: LC10AD
Detector: SPD-10A
Controller: CLASS-LC10
Column: TSK-GEL AMIDE-80 (manufactured and sold by TOSOH, Japan)×2
Size: 4.6 mm×25 cm
Column temperature: 40° C.
Mobile phase: tetrahydrofuran/$H_2O$ (90/10) (v/v)
Flow rate: 1 ml/min
Detection: UV (254 nm)
The amount of a sample per injection: 5 µl Preparation of a Sample The sample for HPLC was prepared as follows unless otherwise specified.

A sample containing $WB_6$ was dissolved into tetrahydrofuran, to thereby obtain a solution having a $WB_6$ concentration of about 0.01% by weight. The obtained solution was used as a sample for HPLC analysis.

(4) An examination under scanning electron microscope (SEM) was conducted under the following conditions.
Apparatus: X-650 type scanning X-ray microanalysis apparatus (manufactured and sold by Hitachi, Ltd., Japan)
Accelerating voltage: 20 kV Preparation of a Sample for SEM Examination A $WB_6$ product was placed on a carbon paste and subjected to gold vacuum deposition so that the thickness of the resultant gold deposition became about 300 angstroms by means of a sputtering apparatus (IB-3 type ion coater; manufactured and sold by Eiko Engineering, Co., Ltd., Japan), to thereby obtain a sample for SEM examination.

EXAMPLE 1

(Method in which a heterogeneous reduction catalyst and a reducing agent are charged into a reactor and preheated to a predetermined reaction temperature, and then, a solution obtained by dissolving $WB_6$ and an acylating agent in a solvent is charged thereinto.)

0.84 g of 10% Pd—C (as a heterogeneous reduction catalyst) was charged into a 100 ml autoclave, and then, the autoclave was purged with hydrogen gas so that the internal pressure of the autoclave became 1.1 kgf/cm². Then, the contents of the autoclave were stirred at a stirring rate of 50 rpm at 60° C. for 2 hours. A solution obtained by dissolving 2.1 g of $WB_6$ (hexabenzylhexaazaisowurtzitane) and 1.82 g of acetic anhydride (as an acylating agent) in 30 ml of DMAc (N,N-dimethylacetamide) (as a solvent) was quickly charged into the autoclave by means of a syringe. Then, immediately, the stirring rate was elevated to 700 rpm while maintaining the temperature at 60° C. and the pressure at 1.1 kgf/cm², and a reaction was performed for 1 hour, to thereby obtain a reaction mixture. Hereinafter, this reaction and the obtained reaction mixture are referred to as "first-stage reaction" and "first-stage reaction mixture", respectively.

The analysis of the obtained first-stage reaction mixture by GC showed that the yields of $WA_4B_2$ (tetraacetyldibenzylhexaazaisowurtzitane) and $WA_4BH$ (tetraacetylbenzylhexaazaisowurtzitane) were 39% and 21%, respectively, (i.e., 60% in total) based on the $WB_6$, and the analysis of the obtained first-stage reaction mixture by HPLC showed that the yield of $WA_4H_2$ (tetraacetylhexaazaisowurtzitane) was 22%, based on the $WB_6$.

After the first-stage reaction, in situ, 30 ml of water were charged into the autoclave containing the first-stage reaction mixture, while introducing hydrogen gas into the autoclave. The internal hydrogen pressure of the autoclave was elevated to 9 kgf/cm², and the reaction temperature was elevated to 90° C., to perform a reaction for 1 hour, thereby obtaining a reaction mixture. Hereinafter, this reaction and the obtained reaction mixture are referred to as "second-stage reaction" and "second-stage reaction mixture", respectively.

The analysis of the obtained second-stage reaction mixture by HPLC showed that the yield of $WA_4H_2$ was 82%, based on the $WB_6$.

EXAMPLE 2

(Method in which a heterogeneous reduction catalyst and a reducing agent are charged into a reactor and preheated to a predetermined reaction temperature, and then, an acylating agent and a solution obtained by dissolving $WB_6$ in a solvent are charged thereinto.)

8.4 g of 10% Pd—C were charged into a 1 liter autoclave, and the autoclave was purged with hydrogen gas so that the internal hydrogen pressure of the autoclave became 1.1 kgf/cm². Then, the contents of the autoclave were heated at 60° C. for 1 hour. To the autoclave were charged, by means of a syringe, 18.2 g of acetic anhydride and a solution obtained by dissolving 21 g of $WB_6$ in 300 ml of DMAc (preheated to 55° C.). Then, immediately, the stirring of the contents of the autoclave was started at a stirring rate of 1500 rpm while maintaining the temperature at 60° C. and the pressure at 1.1 kgf/cm², and a first-stage reaction was performed for 1 hour, to thereby obtain a first-stage reaction mixture.

The analysis of the obtained first-stage reaction mixture by GC showed that the yields of $WA_4B_2$ and $WA_4BH$ were 35% and 26%, respectively., (i.e., 61% in total) based on the $WB_6$, and the analysis of the first-stage reaction mixture by HPLC showed that the yield of $WA_4H_2$ was 29%, based on the $WB_6$.

After the first-stage reaction, in situ, 300 ml of water was charged into the autoclave containing the first-stage reaction mixture while introducing hydrogen gas into the autoclave. The internal hydrogen pressure of the autoclave was elevated to 10 kgf/cm², and the reaction temperature was elevated to 90° C., to perform a second-stage reaction for 1 hour, thereby obtaining a second-stage reaction mixture.

The analysis of the obtained second-stage reaction mixture by HPLC showed that the yield of $WA_4H_2$ was 90%, based on the $WB_6$.

EXAMPLE 3

(Method in which the catalyst contained in a first-stage reaction mixture is filtered off to thereby obtain a filtrate, and a second-stage reaction is performed using a fresh catalyst and the obtained filtrate.)

The first-stage reaction was performed in substantially the same manner as in Example 1. Then, immediately, the obtained first-stage reaction mixture was taken out from the autoclave and the catalyst contained in the first-stage reaction mixture was filtered off, to thereby obtain a filtrate. Using the obtained filtrate, a second-stage reaction was performed as follows.

0.84 g of 10% Pd—C was charged into a 100 ml autoclave, and then, the autoclave was purged with hydrogen gas so that the internal pressure of the autoclave became 1.5 kgf/cm$^2$. Then, the contents of the autoclave were heated at 90° C. for 1 hour. To the autoclave was charged the above-obtained filtrate and 30 ml of water. Then, the internal hydrogen pressure of the autoclave was elevated to 10 kgf/cm$^2$, the stirring of the contents of the autoclave was started at a stirring rate of 700 rpm and the temperature of the contents of the autoclave was elevated to 90° C. over about 8 minutes, to perform a second-stage reaction for 1 hour at 90° C., thereby obtaining a second-stage reaction mixture.

The analysis of the obtained second-stage reaction mixture by HPLC showed that the yield of $WA_4H_2$ was 80%, based on the $WB_6$.

EXAMPLE 4

(Method in which the catalyst contained in a first-stage reaction mixture is filtered off to thereby obtain a filtrate, and a second-stage reaction is performed using a fresh catalyst and the obtained filtrate.)

The first-stage reaction was performed in substantially the same manner as in Example 2. Then, immediately, the obtained first-stage reaction mixture was taken out from the autoclave and the catalyst contained in the first-stage reaction mixture was filtered off, to thereby obtain a filtrate. Using the obtained filtrate, a second-stage reaction was performed as follows.

8.4 g of 10% Pd—C were charged into a 1 liter autoclave, and then, the autoclave was purged with hydrogen gas so that the internal pressure of the autoclave became 1.5 kgf/cm$^2$. Then, the contents of the autoclave were heated at 90° C. for 1 hour. To the autoclave were charged the above-obtained filtrate and 300 ml of water. Then, the internal hydrogen pressure of the autoclave was elevated to 10 kgf/cm$^2$, the stirring of the contents of the autoclave was started at a stirring rate of 1500 rpm and the temperature of the contents of the autoclave was elevated to 90° C. over about 8 minutes to perform a second-stage reaction for 1 hour at 90° C., thereby obtaining a second-stage reaction mixture.

The analysis of the obtained second-stage reaction mixture by HPLC showed that the yield of $WA_4H_2$ was 90%, based on the $WB_6$.

Comparative Example 1

This Comparative Example shows that when there is a contact between $WB_6$ and a heterogeneous reduction catalyst in the absence of at least one of an acylating agent and a reducing agent, the yield of the desired product is markedly lowered.

2.1 g of $WB_6$, 3.15 g of 10% Pd—C, 1.84 g of acetic anhydride and 30 ml of DMAc were charged into a 100 ml autoclave, and the autoclave was purged with nitrogen gas at room temperature. Then, hydrogen gas was introduced into the autoclave so that the internal pressure of the autoclave became 1.1 kgf/cm$^2$. A first-stage reaction was started by elevating the temperature of the contents of the autoclave to 60° C. over about 12 minutes while stirring the contents of the autoclave at a stirring rate of 700 rpm. During the reaction, hydrogen gas was continuously introduced into the autoclave so that the internal pressure of the autoclave was kept at 1.1 kgf/cm$^2$, and the first-stage reaction was performed for 3 hours, to thereby obtain a first-stage reaction mixture. The analysis of the obtained first-stage reaction mixture by GC and HPLC showed that $WA_3B_3$ was completely converted, and that the yields of $WA_4B_2$, $WA_4BH$ and $WA_4H_2$ were 50%, 6% and 4%, respectively, (i.e., 60% in total) based on the $WB_6$.

After the termination of the first-stage reaction, the first-stage reaction mixture was taken out from the autoclave and the catalyst contained in the reaction mixture was filtered off, to thereby obtain a filtrate. Using the obtained filtrate, a second-stage reaction was performed as follows. To a 100 ml autoclave were charged the obtained filtrate, 3.15 g of 10% Pd—C and 30 ml of water. The autoclave was purged with nitrogen gas. Then, hydrogen gas was introduced into the autoclave so that the internal pressure of the autoclave became 3.3 kgf/cm$^2$. The second-stage reaction was started by elevating the temperature of the contents of the autoclave to 130° C. over about 20 minutes while stirring the contents of the autoclave at a stirring rate of 700 rpm. The second-stage reaction was performed for 1 hour at 130° C. while continuously introducing hydrogen gas into the autoclave so that the internal pressure of the autoclave was kept at 3.3 kgf/cm$^2$. The analysis of the second-stage reaction mixture by HPLC showed that the yield of $WA_4H_2$ was 60%, based on the $WB_6$.

Comparative Example 2

This Comparative Example shows that when there is contact between $WB_6$ and a heterogeneous reduction catalyst in the absence of at least one of an acylating agent and a reducing agent, the yield of the desired product is markedly lowered.

2.1 g of $WB_6$, 3.15 g of 10% Pd—C, 1.84 g of acetic anhydride and 30 ml of DMAc were charged into a 100 ml autoclave, and the autoclave was purged with nitrogen gas at room temperature. Then, hydrogen gas was introduced into the autoclave so that the internal pressure of the autoclave became 1.1 kgf/cm$^2$. The stirring of the contents of the autoclave was started at a stirring rate of 50 rpm and the temperature of the contents of the autoclave was elevated to 60° C. over about 12 minutes. Then, immediately, the stirring rate was elevated to 700 rpm, thereby starting a reaction. During the reaction, hydrogen gas was continuously introduced into the autoclave so that the internal pressure of the autoclave was kept at 1.1 kgf/cm$^2$, and the reaction was performed for 3 hours to thereby obtain a reaction mixture. The analysis of the obtained reaction mixture by GC and HPLC showed that the yield of $WA_3B_3$ was 25%, based on the $WB_6$, and the yield of $WA_4B_2$ was 28%, based on the $WB_6$, respectively.

EXAMPLE 5

(Method in which an acylating agent and a reducing agent are charged into a reactor, and then, a solution of $WB_6$ and a catalyst slurry are charged thereinto.)

0.84 g of 10% Pd—C was subjected to reduction treatment in 10 ml of DMAc for 2 hours under conditions wherein the hydrogen pressure was 3 kgf/cm$^2$, the temperature was 60° C. and the stirring rate was 700 rpm, to thereby obtain a catalyst slurry.

1.82 g of acetic anhydride was charged into a 100 ml autoclave and stirred for 30 minutes at a stirring rate of 50 rpm while maintaining the hydrogen pressure at 1.1 kgf/cm$^2$ and the temperature at 60° C. To the autoclave were successively charged, by means of a syringe, a DMAc solution of $WB_6$ (obtained by dissolving 2.1 g of $WB_6$ in 20 ml of DMAc) and the above-obtained catalyst slurry. Then, immediately, the stirring rate was elevated to 700 rpm while maintaining the temperature at 60° C. and the pressure at 1.1 kgf/cm², and a reaction was performed for 1 hour, to thereby obtain a reaction mixture. The analysis of the obtained reaction mixture by GC showed that the yields of $WA_4B_2$ and $WA_4BH$ were 55% and 8%, respectively, (i.e., 63% in total) based on the $WB_6$, and the analysis of the obtained reaction mixture by HPLC showed that the yield of $WA_4H_2$ was 18%, based on the $WB_6$.

EXAMPLE 6

(Method in which a catalyst used in the first-stage reaction is used in the second-stage reaction, and a sequence of the first-stage and second-stage reactions is repeatedly performed using the same catalyst without exchange with fresh catalyst.)

9.8 g of 10% Pd—C (as a heterogeneous reduction catalyst) were dispersed in 200 ml of DMAc (N,N-dimethylacetamide) (as a solvent) to thereby obtain a catalyst slurry, and the obtained slurry was charged into a 2-liter autoclave. The autoclave was purged with nitrogen gas. Then, hydrogen gas (as a reducing agent) was introduced into the autoclave so that the internal pressure of the autoclave became 2 kgf/cm². The contents of the autoclave were stirred at a stirring rate of 300 rpm for 1 hour while maintaining the internal pressure at 2 kgf/cm² and the temperature at 60° C., to thereby effect a reductive treatment of the catalyst contained in the catalyst slurry.

49 g of $WB_6$ (hexabenzylhexaazaisowurtzitane) were dissolved in 500 ml of DMAc at 60° C. to obtain a solution. To the obtained solution were added 42.4 g of acetic anhydride (as an acylating agent), and the resultant liquid mixture was quickly charged into the autoclave containing the catalyst slurry. (When the liquid mixture was charged into the autoclave, the temperature temporarily lowered, but returned to 60° C. in about 4 minutes.) Then, immediately, the stirring rate was elevated to 1,000 rpm while maintaining the temperature at 60° C. and the pressure at 2 kgf/cm², and a first-stage reaction was performed for 1 hour, to thereby obtain a first-stage reaction mixture. The analysis of the first-stage reaction mixture by GC showed that the yields of $WA_4B_2$ (tetraacetyldibenzylhexaazaisowurtzitane) and $WA_4BH$ (tetraacetylbenzylhexaazaisowurtzitane) were 64% and 11%, respectively, (i.e., 75% in total) based on the $WB_6$, and the analysis of the first-stage reaction mixture by HPLC showed that the yield of $WA_4H_2$ (tetraacetylhexaazaisowurtzitane) was 10%, based on the $WB_6$.

After the first-stage reaction, the hydrogen pressure in the 2-liter autoclave containing the first-stage reaction mixture was elevated to 9 kgf/cm², and the reaction temperature was elevated from 60° C. to 90° C. over 30 minutes, to thereby start a second-stage reaction. Introduction of water into the autoclave was started simultaneously with the start of temperature elevation, and 700 ml of water was introduced into the autoclave over 1 hour by means of a pump. The second-stage reaction was continued until 40 minutes after the completion of the introduction of water, to thereby obtain a second-stage reaction mixture. The analysis of the obtained second-stage reaction mixture by HPLC showed that the yield of $WA_4H_2$ was 84%, based on the $WB_6$.

The catalyst was recovered from the second-stage reaction mixture as follows. All of the procedures are conducted in an atmosphere of hydrogen gas unless otherwise specified. The second-stage reaction mixture was transferred to a pressure filtration apparatus, and the catalyst contained in the second-stage reaction mixture was filtered off by pressure filtration, to thereby obtain a filtrate. The catalyst remaining in the pressure filtration apparatus was washed with 500 ml of water, and water was removed from the catalyst by pressure filtration. Then, the catalyst was washed with 500 ml of DMAc in an atmosphere of nitrogen gas, and DMAc was removed by pressure filtration.

A sequence of the first-stage reaction operation, the second-stage reaction operation and the catalyst recovery operation was repeated 10 times in the above-mentioned manner. Each of the second-stage reaction mixtures obtained in the sequences of operations was individually analyzed by HPLC to determine the yield of $WA_4H_2$, based on the $WB_6$. The results show that the values of the $WA_4H_2$ yields of the 1st to the 10th sequences of operations are 84% (1st), 82% (2nd), 85% (3rd), 80% (4th), 79% (5th), 81% (6th), 84% (7th), 83% (8th), 84% (9th) and 80% (10th), respectively.

As apparent from the above, the yield of $WA_4H_2$ did not change even when the same catalyst was repeatedly used without being exchanged with fresh catalysts.

EXAMPLE 7

(Method in which the reaction is repeatedly performed using the same catalyst.)

A reaction was conducted in substantially the same manner as in the first-stage reaction of Example 1, to thereby obtain a reaction mixture. The catalyst contained in the obtained reaction mixture was recovered in substantially the same manner as in the catalyst recovery operation in Example 6, except that each of the amounts of water and DMAc was 50 ml.

A sequence of the above-mentioned reaction operation and the catalyst recovery operation was repeated 5 times in the above-mentioned manner. Each of the reaction mixtures obtained in the sequences of operations was individually analyzed by GC to determine the yield of the sum of $WA_4B_2$ and $WA_4BH$, based on the $WB_6$, and individually analyzed by HPLC to determine the yield of $WA_4H_2$, based on the $WB_6$. The results are shown in Table 1.

TABLE 1

| Operation | Yield (%) of $WA_4B_2$ + $WA_4BH$ | Yield (%) of $WA_4H_2$ |
| --- | --- | --- |
| 1st | 60 | 20 |
| 2nd | 57 | 21 |
| 3rd | 57 | 19 |
| 4th | 60 | 17 |
| 5th | 58 | 23 |

As apparent from the above, the yield of tetraacetylhexaazaisowurtzitane derivatives did not change even when the same catalyst was repeatedly used in the reaction.

EXAMPLE 8

(Method in which the reaction is continuously performed using the same catalyst (continuous reaction wherein a part of a reaction mixture obtained by the reaction is subjected to filtration in a reactor and the resultant filtrate containing reaction products is intermittently withdrawn from the reactor, while intermittently charging a raw material solution into the reactor).)

As a reactor, use was made of a 200 ml autoclave provided with a sintered metal filter (pore diameter: 2 μm) and a pipe for withdrawing a liquid which is obtained from the reaction mixture by filtration through the sintered metal filter. By using this type of autoclave, it becomes possible to filter a reaction mixture (which is obtained by a reaction catalyzed by a heterogeneous reduction catalyst in this autoclave), and withdraw the resultant filtrate (that is, the catalyst can be filtered off in the autoclave without removing the catalyst outside of the autoclave, so that the reaction can be continued using the same catalyst.

Using the above-mentioned 200 ml autoclave, a continuous reaction was conducted, wherein a part of a reaction mixture obtained by the reaction is subjected to filtration in a reactor and the resultant filtrate containing reaction products is intermittently withdrawn from the reactor, while intermittently charging a raw material solution into the reactor.

14.7 g of $WB_6$ were dissolved in 210 ml of DMAc at about 60° C., and the resultant solution was then allowed to be cooled to room temperature, and 12.74 g of acetic anhydride were added, to thereby obtain a raw material solution.

A reaction was performed in substantially the same manner as in the first-stage reaction in Example 1, except that the amounts of $WB_6$, acetic anhydride, solvent and catalyst were, respectively, four times the amounts used in Example 1, and that the hydrogen pressure was 4 kgf/cm² and the stirring rate was 1,500 rpm. After 1 hour from the start of the reaction, a part of the resultant reaction mixture was withdrawn from the autoclave through the sintered metal filter so that 40 g of a filtrate were obtained while maintaining the hydrogen pressure at 4 kgf/cm² and the stirring rate at 1,500 rpm. Then, 40 g of the raw material solution were charged into the autoclave. The operation for charging the raw material solution into the autoclave was conducted while maintaining the hydrogen pressure, the stirring rate, and the temperature of the reaction mixture so that the reaction can be continued.

40 Minutes after charging the raw material solution into the autoclave, a sequence of the reaction, the filtration of a part of the reaction mixture, the withdrawal of the filtrate from the autoclave and the charging of the raw material solution into the autoclave was repeated while continuing the reaction. This sequence of the operations was repeated 11 times in the same manner as described above, while continuing the reaction in the autoclave. Each of the filtrates obtained in the sequences of operations was individually analyzed by GC to determine the yield of the sum of $WA_4B_2$ and $WA_4BH$, based on the $WB_6$, and also analyzed by HPLC to determine the yield of $WA_4H_2$, based on the $WB_6$. The results are shown in Table 2.

TABLE 2

| Operation number | Yield (%) of $WA_4B_2$ + $WA_4BH$ | Yield (%) of $WA_4H_2$ |
| --- | --- | --- |
| 1st | 68 | 15 |
| 2nd | 72 | 13 |
| 3rd | 69 | 13 |
| 4th | 70 | 12 |
| 5th | 71 | 10 |
| 6th | 68 | 13 |
| 7th | 73 | 11 |
| 8th | 75 | 9 |
| 9th | 74 | 10 |
| 10th | 72 | 8 |
| 11th | 73 | 9 |

As apparent from the above, the yield of tetraacetylhexaazaisowurtzitane derivatives did not change even when the same catalyst was repeatedly used in the reaction.

EXAMPLE 9
(Method in which the reaction is continuously performed using the same catalyst (continuous reaction wherein a part of a reaction mixture obtained by the reaction is subjected to filtration in a reactor and the resultant filtrate containing reaction products is continuously withdrawn from the reactor, while continuously charging a raw material solution thereinto).)

Using the same 200 ml autoclave as used in Example 8, a continuous reaction was conducted, wherein a part of the reaction mixture obtained by the reaction is subjected to filtration in a reactor and the resultant filtrate containing reaction products is continuously withdrawn from the reactor, while continuously charging a raw material solution into the reactor.

A reaction was performed in substantially the same manner as in the first-stage reaction in Example 1, except that the amounts of $WB_6$, acetic anhydride, solvent and catalyst were, respectively, four times the amounts used in Example 1, and that the hydrogen pressure was 4 kgf/cm² and the stirring rate was 1,500 rpm. After 1 hour from the start of the reaction, a part of the resultant reaction mixture was continuously withdrawn from the autoclave through the sintered metal filter so that a filtrate was continuously withdrawn from the pipe at a rate of 0.33 g/min, while maintaining the hydrogen pressure at 4 kgf/cm², the stirring rate at 1,500 rpm, and the temperature of the reaction mixture, and while charging the raw material solution into the autoclave at a rate of 0.33 g/min. This continuous reaction was performed for 20 hours, and a part of the filtrate withdrawn from the autoclave was taken for GC and HPLC analyses every 2 hours. Each of the filtrates taken was individually analyzed by GC to determine the yield of the sum of $WA_4B_2$ and $WA_4BH$, based on the $WB_6$, and also analyzed by HPLC to determine the yield of $WA_4H_2$, based on the $WB_6$. The results are shown in Table 3.

TABLE 3

| Sampling time (hr) | Yield (%) of $WA_4B_2$ + $WA_4BH$ | Yield (%) of $WA_4H_2$ |
| --- | --- | --- |
| 0 | 67 | 12 |
| 2 | 68 | 14 |
| 4 | 65 | 14 |
| 6 | 65 | 16 |
| 8 | 69 | 14 |
| 10 | 69 | 12 |
| 12 | 68 | 14 |
| 14 | 70 | 13 |
| 16 | 71 | 11 |
| 18 | 67 | 12 |
| 20 | 69 | 11 |

As apparent from the above, the yield of tetraacetylhexaazaisowurtzitanes did not change even when the reaction is conducted in a continuous manner.

EXAMPLE 10
(Method in which a second-stage reaction is repeatedly conducted using the same catalyst.)

All of the filtrates (each of which was the reaction mixture wherein the catalyst was filtered off) obtained in Example 8, were combined and allowed to stand at room temperature, to thereby obtain a slurry containing deposited $WA_4B_2$, $WA_4BH$, $WA_4H_2$ and the like. Using the obtained slurry, a second-stage reaction was performed as follows.

0.84 g of 10% Pd—C was charged into a 100 ml autoclave, and then, hydrogen gas was introduced into the autoclave so that the internal pressure of the autoclave became 1.1 kgf/cm². The contents of the autoclave were stirred for 1 hour at a stirring rate of 50 rpm while maintaining the pressure at 1.1 kgf/cm² and the temperature at 90° C. A mixture of 30 g of the above-mentioned slurry and 10.5 g of water was quickly charged into the autoclave by means of a syringe. Then, immediately, the pressure and the stirring rate were elevated to 10 kgf/cm$^2$ and 700 rpm, respectively, to perform a second-stage reaction for 1 hour at a temperature of 90° C. under a pressure of 10 kgf/cm$^2$, thereby obtaining a second-stage reaction mixture. Then, immediately, the second-stage reaction mixture was subjected to filtration, to thereby obtain a filtrate and a catalyst.

A sequence of the second-stage reaction operation and filtration operation was repeated 5 times in the above-mentioned manner. Each of the filtrates obtained in the sequences of operations was individually analyzed by GC to determine the conversion of the sum of WA$_4$B$_2$ and WA$_4$BH, and also analyzed by HPLC to determine the yield of WA$_4$H$_2$, based on the sum of WA$_4$B$_2$ and WA$_4$BH. The results are shown in Table 4.

TABLE 4

| Operation | Yield (%) of WA$_4$B$_2$ + WA$_4$BH | Yield (%) of WA$_4$H$_2$ |
| --- | --- | --- |
| 1st | 100 | 99 |
| 2nd | 100 | 100 |
| 3rd | 100 | 98 |
| 4th | 100 | 100 |
| 5th | 100 | 97 |

As apparent from the above, the yield of tetraacetylhexaazaisowurtzitanes did not change even when the same catalyst was repeatedly used in the reaction.

EXAMPLE 11
(Method in which a second-stage reaction is continuously performed using the same catalyst.)

The filtrate, which was obtained in Example 9 (the reaction mixture) wherein the catalyst was filtered off, was allowed to stand at room temperature, to thereby obtain a slurry containing deposited WA$_4$B$_2$, WA$_4$BH, WA$_4$H$_2$ and the like. 400 g of the obtained slurry and 140 g of water were mixed together to thereby obtain a raw material solution. The analysis of the raw material solution by GC showed that the amount of the sum of WA$_4$B$_2$ and WA$_4$BH contained in the raw material solution was 13.9 g and the analysis of the raw material solution by HPLC showed that the amount of WA$_4$H$_2$ contained in the raw solution mixture was 1.7 g.

6.72 g of 10% Pd—C were charged into the 200 ml autoclave used in Example 8, and then, hydrogen gas was introduced into the autoclave so that the internal pressure of the autoclave became 1.1 kgf/cm$^2$. The contents of the autoclave were stirred for 1 hour at a stirring rate of 50 rpm while maintaining the pressure at 1.1 kgf/cm$^2$ and the temperature at 90° C. 120 g of the raw material solution were quickly charged into the autoclave by means of a syringe. Then, immediately, the stirring rate and the pressure were elevated to 1,400 rpm and 10 kgf/cm$^2$, respectively, to thereby perform a second-stage reaction for 30 minutes. After 30 minutes from the start of the reaction, a part of the reaction mixture was continuously withdrawn from the autoclave through the sintered metal filter so that a filtrate was continuously withdrawn from the pipe at a rate of 0.3 ml/min, while maintaining the hydrogen pressure at 1.1 kgf/cm$^2$, the stirring rate at 1400 rpm and the temperature of the reaction mixture at 90° C., and while charging the raw material solution into the autoclave at a rate of 0.3 ml/min. This continuous reaction was performed for 20 hours, and a part of the filtrate withdrawn from the autoclave was taken for GC and HPLC analyses every 2 hours. Each of the sampled filtrates taken was individually analyzed by GC to determine the conversion of the sum of WA$_4$B$_2$ and WA$_4$BH, and also analyzed by HPLC to determine the yield of WA$_4$H$_2$, based on the sum of WA$_4$B$_2$ and WA$_4$BH. The results are shown in Table 5.

TABLE 5

| Sampling time (hr) | Conversion (%) of WA$_4$B$_2$ + WA$_4$BH— | Yield (%) of WA$_4$H$_2$ |
| --- | --- | --- |
| 0 | 100 | 100 |
| 2 | 97 | 97 |
| 4 | 99 | 98 |
| 6 | 96 | 95 |
| 8 | 97 | 95 |
| 10 | 99 | 98 |
| 12 | 98 | 96 |
| 14 | 95 | 95 |
| 16 | 97 | 97 |
| 18 | 97 | 95 |
| 20 | 99 | 98 |

As apparent from the above, the yield of tetraacetylhexaazaisowurtzitanes did not change even when the reaction is conducted in a continuous manner.

Comparative Example 3

This Comparative Example 3 shows that when the first-stage reaction mixture is subjected to the second-stage reaction without an introduction of hydrogen gas into the reactor, the reaction rate of the second-reaction becomes markedly low.

A first-stage reaction was conducted in substantially the same manner as in Example 6, to thereby obtain a first-stage reaction mixture. The analysis of the obtained first-stage reaction mixture by GC showed that the yields of WA$_4$B$_2$ and WA$_4$BH were 65% and 7%, respectively, (i.e., 72% in total) based on the WB$_6$, and the analysis of the obtained first-stage reaction mixture by HPLC showed that the yield of WA$_4$H$_2$ was 10%, based on the WB$_6$.

After the first-stage reaction, nitrogen gas was introduced into the autoclave so that the internal pressure of the autoclave became 9 kgf/cm$^2$. The temperature of the contents of the autoclave was elevated from 60° C. to 90° C. over 30 minutes. Introduction of water into the autoclave was started simultaneously with the start of the temperature elevation, and 700 ml of water was introduced into the autoclave over 1 hour by means of a pump. Then, hydrogen gas was introduced into the autoclave so that the internal pressure became 9 kgf/cm$^2$, and a second-stage reaction was performed for 2 hours, to thereby obtain a second-stage reaction mixture.

The analysis of the obtained second-stage reaction mixture by GC showed that the yields of WA$_4$B$_2$ and WA$_4$BH were 42% and 3%, respectively, (i.e., 45% in total) based on the WB$_6$, and the analysis of the obtained first-stage reaction mixture by HPLC showed that the yield of WA$_4$H$_2$ was 30%, based on the WB$_6$.

As apparent from the above, when the introduction of hydrogen gas into the autoclave is interrupted while changing the reaction conditions between the end of the first-stage reaction and the start of the second-stage reaction, the reaction rate of the second-stage reaction becomes markedly low.

Comparative Example 4

This Comparative Example shows that when the value of K (flow rate for charging WB$_6$)/Q (amount of catalyst) is 0.5 or more, the yield Of the desired product becomes markedly low.

A reaction was conducted in substantially the same manner as in Example 9, except that each of the rate for charging the raw material solution and the rate for withdrawing the filtrate (reaction mixture wherein the catalyst was filtered off) was 30 ml/min. The reaction was continuously performed for 2 hours. A part of the filtrate withdrawn from the autoclave was taken for GC and HPLC analyses after 30, 60 and 120 minutes from the start of the reaction. The analyses of the filtrates withdrawn from the autoclave showed that both of the yield of $WA_4B_2$ and the yield of $WA_4BH$ were 10% or less, based on the $WB_6$, in all of the filtrates obtained after 30 minutes from the start of the reaction.

EXAMPLE 12

(Method in which a reaction is conducted in the presence of a carboxylic acid, wherein the content of the carboxylic acid in the solvent used for the reaction is about 10% by weight.)

This Example shows that even when the reaction system contains a carboxylic acid (which is derived from an acylating agent used in the reaction) in a concentration of about 10% by weight, based on the weight of the solvent used for the reaction, the method of the present invention is not adversely affected.

A reaction was conducted in substantially the same manner as in the first-stage reaction in Example 1, except that 3.0 g of acetic acid were added to the solution obtained by dissolving $WB_6$ and acetic anhydride in DMAC, just before the solution was charged into the autoclave. The analysis of the obtained reaction mixture by GC showed that the yields of $WA_4B_2$ and $WA_4BH$ were 53% and 9%, respectively, (i.e., 62% in total) based on the $WB_6$, and the analysis of the obtained reaction mixture by HPLC showed that the yield of $WA_4H_2$ was 17%, based on the $WB_6$.

Comparative Example 5

This Comparative Example shows that when a solvent for a reaction contains acetic acid in a concentration of more than 10% by weight, based on the weight of the solvent, the yield of the desired product becomes markedly low.

A reaction was conducted in substantially the same manner as in Example 12 except that 6.0 g (instead of 3.0 g) of acetic acid were used. The analysis of the obtained reaction mixture by GC showed that the yield of the sum of $WA_4B_2$ and $WA_4BH$ was 40% or less, based on the $WB_6$, and the analysis of the obtained first-stage reaction mixture by HPLC showed that the yield of $WA_4H_2$ was 5% or less, based on the $WB_6$.

EXAMPLE 13

(Method in which $WB_6$ is used in a high concentration.)

This Example shows that the method of the present invention can be conducted even when the reaction system contains $WB_6$ (as a raw material) in a concentration as high as 14% by weight, based on the solvent.

A reaction was conducted in substantially the same manner as in the first-stage reaction in Example 1 except that 4.2 g (instead of 2.1 g) of $WB_6$ were used, the internal temperature of the autoclave before charging DMAc solution of $WB_6$ and acetic anhydride into the autoclave was 55° C. (instead of 60° C.), and 2.1 g of 10% Pd—C were used (instead of 0.84 g), to thereby obtain a reaction mixture. The analysis of the obtained reaction mixture by GC showed that the yields of $WA_4B_2$ and $WA_4BH$ were 39% and 19%, respectively, (i.e., 58% in total) based on the $WB_6$, and the analysis of the obtained first-stage reaction mixture by HPLC showed that the yield of $WA_4H_2$ was 20%, based on the $WB_6$.

Reference Example 1

(Solubilities of various types of acyl group-containing hexaazaisowurtzitane derivatives in various solvents.)

The solubilities of various types of acyl group-containing hexaazaisowurtzitane derivatives in various solvents were examined. The results are shown in Table 6.

TABLE 6

Solubilities of various types of acyl group-containing hexaazaisowurtzitane derivatives in various solvents at room temperature

| | | | $WA_4H_2$ | $WA_4B_2$ | $WA_6$ | $WA_4R_2$ |
|---|---|---|---|---|---|---|
| First solvent | | Water | >3% | <0.1% | >1% | >3% |
| | | Acetic acid | >1% | >10% | >2% | >4% |
| Second solvent | Amide group-containing solvents | DMAc | <0.1% | >0.2% | >1% | >3% |
| | | DMF | <0.1% | >0.2% | >1% | >3% |
| | | DMI | <0.1% | >0.2% | >1% | >3% |
| | | NMP | <0.1% | >0.2% | >1% | >3% |

The abbreviations used in Table 6 represent the compounds as specified below.
$WA_4H_2$: tetraacetylhexaazaisowurtzitane
$WA_4B_2$: tetraacetyldibenzylhexaazaisowurtzitane
$WA_6$: hexaacetylhexaazaisowurtzitane
$WA_4R_2$: tetraacetyldiethylhexaazaisowurtzitane
DMAc: N,N-dimethylacetamide
DMF: N,N-dimethylformamide
DMI: 1,3-dimethyl-2-imidazolidone
NMP: N-methyl-2-pyrrolidone Reference Example 2

(Distillative crystal deposition of $WA_4H_2$.)

1 g of $WA_4H_2$ was dissolved in a mixed solvent of first and second solvents to obtain a solution. Then, the first solvent was distilled off from the solution to deposit crystals of $WA_4H_2$. The respective amounts (g) of the first and second solvents employed and the results of the distillative crystal deposition are shown in Table 7. In Reference Example 2, the distillation for crystal deposition was performed to an extent such that the content of the first solvent became 1% by weight or less, based on the total weight of the first and second solvents.

TABLE 7

Results of crystal deposition of $WA_4H_2$ (tetraacetylhexaazaisowurtzitane)

| First solvent | | Second solvent | | Results |
|---|---|---|---|---|
| Solvent | Amount (g) | Solvent | Amount (g) | Yield (%) |
| Water | 40 | DMAc | 20 | 98 |
| Acetic acid | 40 | DMAc | 20 | 98 |
| Water | 40 | DMF | 20 | 97 |
| Water | 40 | DMI | 20 | 96 |
| Water | 40 | NMP | 20 | 97 |

The abbreviations used in Table 7 represent the compounds as specified below.
DMAc N,N-dimethylacetamide
DMF: N,N-dimethylformamide
DMI: 1,3-dimethyl-2-imidazolidone
NMP: N-methyl-2-pyrrolidone

EXAMPLE 14

(Method in which the second-stage reaction mixture (which is produced in a batchwise manner by effecting an in situ reaction of the first-stage reaction mixture) is subjected to distillative crystal deposition.)

The second-stage reaction mixture obtained in Example 2 was subjected to distillative crystal deposition in the following manner.

300 ml of the second-stage reaction mixture obtained in Example 2 were subjected to filtration to remove the catalyst contained in the reaction mixture, thus obtaining a filtrate. The obtained filtrate was charged into a 500 ml egg plant flask and subjected to distillation (50° C., 10 mmHg) using a rotary evaporator equipped with a constant temperature bath, a vacuum pump and a vacuum controller, to thereby remove about 150 ml of low boiling point fractions (such as water and toluene) having a boiling point which is lower than that of DMAc. After the distillation, the egg plant flask was disconnected from the rotary evaporator, and the resultant distillation residue in the egg plant flask was allowed to cool to room temperature and stand at room temperature for 12 hours, thereby depositing solids.

The deposited solids were collected by suction filtration and then washed with about 10 ml of DMAc to thereby obtain a wet solid substance. The wet solid substance was subjected to drying by means of a vacuum dryer (70° C., 1 mmHg or less) to thereby obtain 4.4 g of $WA_4H_2$ as a white solid (crystal deposition yield: 98%; purity: 98% (determined by HPLC)).

EXAMPLE 15
(Method in which the second-stage reaction mixture (which is produced in a continuous manner by continuously effecting the first-stage reaction) is subjected to distillative crystal deposition.)

The filtrate (the reaction mixture wherein the catalyst was filtered off) obtained in Example 11 was subjected to distillative crystal deposition in the following manner.

The filtrate (the reaction mixture wherein the catalyst was filtered off) was analyzed by HPLC. As a result, it was found that the content of $WA_4H_2$ in the filtrate was 1.90 g/100 ml. 100 ml of the filtrate were charged into a 300 ml egg plant flask and subjected to distillation in substantially the same manner as in Example 14 using a rotary evaporator, to thereby remove about 28 ml of low boiling fractions (such as toluene and water) having a boiling point which is lower than that of DMAc. After the distillation, the egg plant flask was disconnected from the rotary evaporator, and the resultant distillation residue in the egg plant flask was allowed to cool to room temperature and stand for 12 hours at room temperature, thereby depositing solids.

The deposited solids were collected by suction filtration and then washed with about 5 ml of DMAc to thereby obtain a wet solid substance. The wet solid substance was subjected to drying by means of a vacuum dryer (70° C., 1 mmHg or less) to thereby obtain 1.84 g of $WA_4H_2$ as a white solid (crystal deposition yield: 97%; purity: 99% (determined by HPLC)).

EXAMPLE 16
(Method in which a crystallization solvent is recycled (NaOH-neutralization method).)

In Example 14, when the deposited $WA_4H_2$ was collected by suction filtration after performing the distillative crystal deposition of $WA_4H_2$, a filtrate containing DMAc was also obtained. The analysis of the filtrate by GC showed that the content of acetic acid in the filtrate was 2.30 g, relative to 100 ml of the filtrate.

To 100 ml of the above-mentioned filtrate were added 20 ml of a 2N NaOH aqueous solution while stirring for 30 minutes, to thereby neutralize the acetic acid contained in the filtrate. Then, the resultant mixture was subjected to distillation, to thereby obtain 95 ml of a distillate composed mainly of the DMAc. The content of acetic acid in the obtained distillate was less than 0.5% by weight.

The above quantitative analyses of the contents of acetic acid in the above filtrate and distillate were conducted by GC under the following conditions using the below-described apparatus.

CONDITIONS FOR GC ANALYSIS

GC apparatus: GC-10 type gas chromatography (manufacture and sold by Shimadzu Corporation, Japan)
Column: Capillary column, DB-1 (manufactured and sold by J & W Scientific Co., Ltd., U.S.A.)
Inner diameter: 0.25 mm
Length: 30 m
Thickness of film coated on the inner wall of the capillary column: 0.25 μm
Detection: flame ionization detector (FID)
Temperature: 60° C. (3 min)
  Column: elevated to 300° C. (temperature elevation rate: 10° C./min)
  300° C. (5 min)
  Inlet: 300° C.
  Detector: 300° C.
Carrier gas: $N_2$ (flow rate: 100 ml/min; and column internal pressure: 100 kpa)
The amount of a sample per injection: 5 μl (obtained filtrate or distillate per se)

EXAMPLE 17
(Method in which a crystallization solvent is recycled (basic Mg-neutralization method).)

In Example 14, when the deposited $WA_4H_2$ was collected by suction filtration after performing the distillative crystal deposition of $WA_4H_2$, a filtrate containing DMAC was also obtained. The analysis of the filtrate by GC showed that the content of acetic acid in the filtrate was 2.30 g, relative to 100 ml of the filtrate.

To 100 ml of the above-mentioned filtrate was added $Mg(OH)_2$ so that the pH value of the filtrate became 8.00, to thereby obtain a slurry containing $Mg(OAc)_2$. (About 2.4 g of $Mg(OH)_2$ was required for adjusting the pH value of the filtrate to 8.00.) The obtained slurry was subjected to distillation using a still under conditions such that the temperature was 100° C. and the pressure was 50 Torr, thereby obtaining 95 ml of a distillate which is composed mainly of the DMAc. The content of acetic acid in the obtained distillate was 0.5% by weight or less. The quantitative analysis of acetic acid was conducted by GC under the same conditions as described in Example 16. When the inside of the still was observed after distillation of DMAc, only a pale brown liquid was found in the still, and no substance adhering to the inner wall of the still was observed.

Reference Example 3
(Production of crude $WB_6$ by a conventional method.)

Into a 2-liter separable flask provided with a stirrer, a thermometer, a condenser and a dropping funnel were charged 1.1 liter of acetonitrile, 100 ml of distilled water, 117.9 g (1.1 mol) of benzylamine and 4.6 ml (0.11 mol) of formic acid, and the resultant mixture in the flask was cooled to 10° C. by means of a constant temperature bath. Then, 72.5 g of a 40% aqueous solution of glyoxal (containing 0.5 mol of glyoxal) was gradually added to the mixture by means of the dropping funnel over 1 hour while stirring and while maintaining the temperature of the mixture at 10° C. After the addition of the solution of glyoxal, the resultant mixture was heated to 25° C. while stirring, and then, further stirred for 18 hours to thereby effect a reaction. As a result, a white solid was deposited from the resultant yellow reaction mixture. The reaction mixture containing the white solid was subjected to suction filtration to thereby collect the solid, and then, the collected solid was washed with a mixed solvent (cooled to 0° C.) of 275 ml of acetonitrile and 25 ml of distilled water. The washed solid was dried overnight at room temperature under reduced pressure, to thereby obtain 92.34 g of crude $WB_6$ (hexabenzylhexaazaisowurtzitane). The analysis of the obtained crude $WB_6$ by HPLC showed that the purity of the crude $WB_6$ was 90.2%.

The above-obtained crude $WB_6$ (in a solid form) was examined by means of a scanning electron microscope (SEM) to obtain a SEM photomicrograph (×200), and the obtained SEM is shown in FIG. 1.

Reference Example 4
(Purification of crude $WB_6$ by a conventional recrystallization method.)

The conventional recrystallization method for purifying $WB_6$ which uses a small amount of crystallization solvent is described below.

16.58 g of the crude $WB_6$ (purity: 90.2%) obtained in Reference Example 3 and 1 liter of acetonitrile were charged into a 2-liter beaker. The resultant mixture in the beaker was heated to 90° C. by means of a constant temperature bath while stirring, to thereby completely dissolve the $WB_6$ in the acetonitrile. After dissolving the $WB_6$ in the acetonitrile, the temperature of the resultant solution of $WB_6$ was lowered to 20° C., and the solution was stirred for 4 hours while maintaining the temperature of the solution at 20° C., to thereby recrystallize $WB_6$. The recrystallized $WB_6$ was collected by suction filtration and dried, to thereby obtain 14.52 g of white crystals of $WB_6$.

The analysis of the obtained crystals of $WB_6$ by HPLC showed that the purity of the crystals of $WB_6$ was 92.7%.

Figure 2:
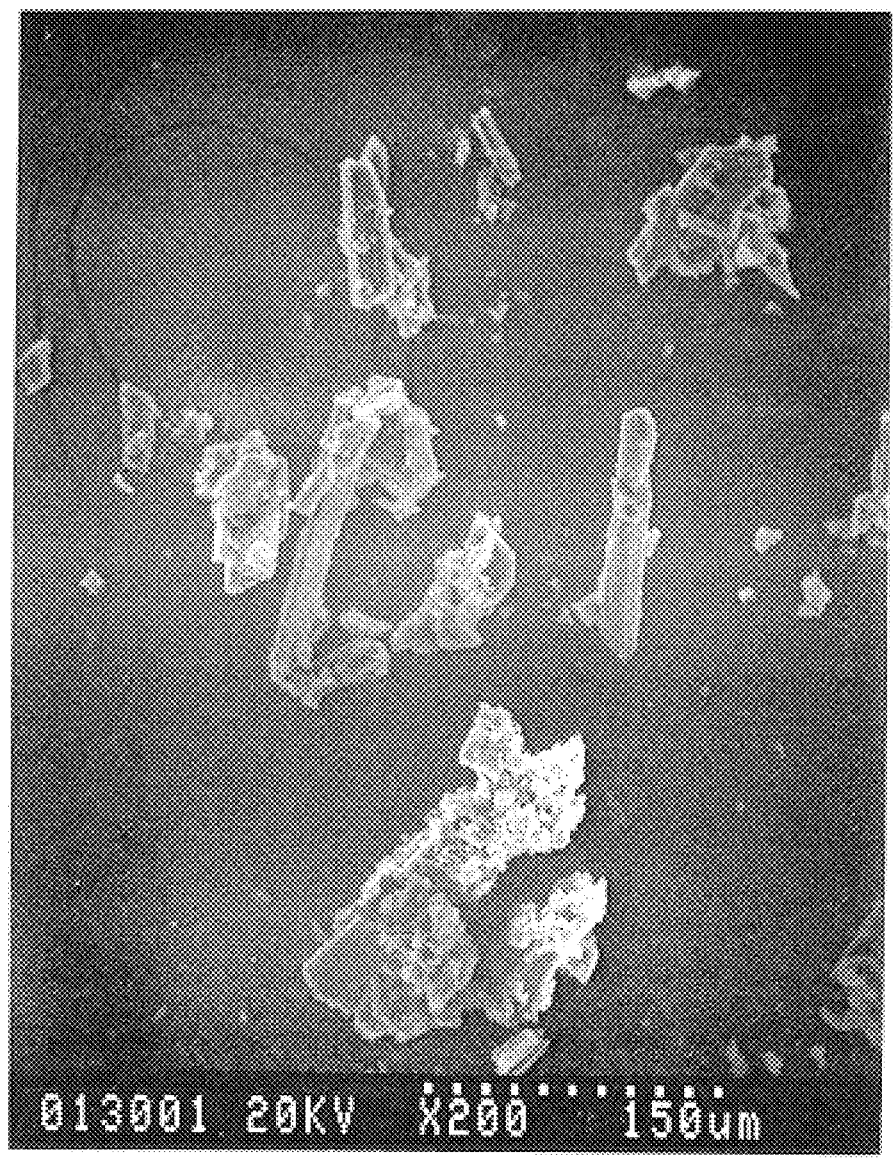
FIG. 2 is an SEM photomicrograph (×200) of the crystals of hexabenzylhexaazaisowurtzitane obtained in Reference Example 4 by subjecting the crude hexabenzylhexaazaisowurtzitane obtained in Reference Example 3 to recrystallization.

The crystals of $WB_6$ obtained above were examined by means of SEM to obtain a SEN photomicrograph (×200), and the obtained SEM photomicrograph is shown in FIG. 2. As is clearly seen from FIG. 2, the purity of the crystals of $WB_6$ obtained by the conventional purification method was disadvantageously low.

Reference Example 5
(Solubilities of $WB_6$ in various types of organic solvents.)

Using the crude $WB_6$ obtained in Reference Example 3, the solubilities (H) of $WB_6$ in various organic solvents and the solubilities (I) of impurities (contained in the crude $WB_6$) in various organic solvents were determined as follows.

10 ml of an organic solvent and the crude $WB_6$ obtained in Reference Example 3 were charged into a beaker, and the resultant mixture was stirred at a predetermined temperature for 1 hour, to thereby obtain a slurry. (The crude $WB_6$ was used in an amount such that a part of the $WB_6$ remained dispersed in the organic solvent even after stirring the mixture for 1 hour at the predetermined temperature.) The obtained slurry was filtered to thereby obtain a filtrate. A part of the filtrate was taken for HPLC analysis. A sample for HPLC was prepared by diluting the taken filtrate with a mixed solvent of tetrahydrofuran and water (90/10, v/v) so that the $WB_6$ content of the resultant solution became about 0.01% by weight. The sample was analyzed by HPLC, thereby obtaining a chromatogram. The chromatogram showed one peak corresponding to $WB_6$ and another peak corresponding to the impurities. The retention time of $WB_6$ was 2.4 minutes, and the retention time of the impurities was 2.2 minutes. The $WB_6$ content of the filtrate was determined from the obtained chromatogram. The determined $WB_6$ content of the filtrate was taken as a solubility of $WB_6$ in the organic solvent at the predetermined temperature.

The solubility of the impurities was determined as follows. To the above-obtained filtrate was added a predetermined amount of the crude $WB_6$ (containing impurities) obtained in Reference Example 3. Then, the resultant mixture was filtered in the above-mentioned manner and the resultant filtrate was analyzed by HPLC in the above-mentioned manner. The addition of crude $WB_6$ to the filtrate, the filtration, and the analysis by HPLC were repeated until the ratio of the intensity of the peak corresponding to the impurities relative to the peak corresponding to $WB_6$ in the chromatogram no longer increased even when the crude $WB_6$ was added to the filtrate. The content of the impurities in the filtrate was determined from the chromatogram showing the peak corresponding to the impurities, wherein the ratio of the intensity of the peak corresponding to the impurities relative to the peak corresponding to $WB_6$ is maximum, and the determined content of the impurities in the filtrate was taken as the solubility of impurities in the organic solvent at the predetermined temperature.

Using the solubility (H) of $WB_6$ and the solubility (I) of the impurity determined by HPLC analysis, calculation of solubility ratio (P) was made by the following formula:

$$P=H/I$$

wherein H represents the solubility (g/l) of $WB_6$ in an organic solvent; and I represents the solubility (g/l) of the impurities (detected by HPLC analysis) in the organic solvent.

The results are shown in Table 8.

TABLE 8

| Organic solvent | Temperature ° C. | Solubility (H) (g/1) of $WB_6$[1)] | Solubility (I) (g/1) of Impurities | Solubility ratio (P) (P = H/I) |
|---|---|---|---|---|
| Acetonitrile | 5 | 0.42 | 0.11 | 3.8 |
|  | 20 | 0.82 | 0.14 | 5.9 |
|  | 40 | 1.36 | 0.25 | 5.4 |
|  | 60 | 5.36 | 0.88 | 6.1 |
| Ethanol | 5 | 0.12 | 0.14 | 0.9 |
|  | 20 | 0.20 | 0.15 | 1.4 |
|  | 40 | 0.32 | 0.22 | 1.5 |
|  | 60 | 0.98 | 0.69 | 1.4 |

TABLE 8-continued

| Organic solvent | Temperature °C. | Solubility (H) (g/1) of WB$_6$[1] | Solubility (I) (g/1) of Impurities | Solubility ratio (P) (P = H/I) |
|---|---|---|---|---|
| DMAc[2] | 5 | 30.04 | 3.12 | 9.6 |
|  | 20 | 50.35 | 2.49 | 20.2 |
|  | 40 | 115.82 | 7.56 | 15.3 |
|  | 60 | 233.50 | 12.10 | 19.3 |
| Ethyl acetate | 5 | 12.43 | 0.65 | 19.2 |
|  | 40 | 52.02 | 5.65 | 10.3 |
| Mixed solvent[3] | 5 | 2.46 | 0.94 | 2.6 |

[1]Hexabenzylhexaazaisowurtzitane
[2]N,N-dimethylacetamide
[3]Mixed solvent of ethyl acetate/ethanol (50/50) (v/v)

Reference Example 6
(Purification of crude WB$_6$ by an improved recrystallization method.)

The improved recrystallization method for purifying WB$_6$ which uses a large amount of crystallization solvent is described below.

3.9 g of the crude WB$_6$ (purity: 90.2%) obtained in Reference Example 3 and 1 liter of acetonitrile were charged into a 2-liter beaker. The resultant mixture in the beaker was heated to 90° C. by means of a constant temperature bath while stirring, to thereby completely dissolve the WB$_6$ in the acetonitrile. After dissolving the WB$_6$ in the acetonitrile, the temperature of the resultant solution of WB$_6$ was lowered to 20° C., and the solution was stirred for 4 hours while maintaining the temperature of the solution at :20° C., to thereby recrystallize WB$_6$. The recrystallized WB$_6$ was collected by suction filtration and dried, to thereby obtain 2.5 g of white crystals of WB$_6$.

The analysis of the obtained crystals of WB$_6$ by HPLC showed that the purity of the crystals of WB$_6$ was 100%.

Reference Example 7
(Purification of crude WB$_6$ by an improved recrystallization method.)

50 g of the crude WB$_6$ (purity: 90.2%) obtained in Reference Example 3 and 1 liter of ethyl acetate were charged into a 2-liter beaker. The resultant mixture in the beaker was heated to 60° C. By means of a constant temperature bath while stirring, to thereby completely dissolve the WB$_6$ in the ethyl acetate. After dissolving the WB$_6$ in the ethyl acetate, the temperature of the resultant solution of WB$_6$ was lowered to 15° C., and the solution was stirred for 4 hours while maintaining the temperature of the solution at 15° C., to thereby recrystallize WB$_6$. The recrystallized WB$_6$ was collected by suction filtration and subjected to drying, to thereby obtain 22.6 g of white crystals of WB$_6$.

The analysis of the obtained crystals of WB$_6$ by HPLC showed that the purity of the crystals of WB$_6$ was 1005.

Reference Example 8
(Purification of crude WB$_6$ by an improved recrystallization method.)

25 g of the crude WB$_6$ (purity: 90.2%) obtained in Reference Example 3 and a mixed solvent of 500 ml of ethyl acetate and 500 ml of ethanol were charged into a 2-liter beaker. The resultant mixture in the beaker was heated to 60° C. by means of a constant temperature bath while stirring, to thereby completely dissolve the WB$_6$ in the mixed solvent. After dissolving the WB$_6$ in the mixed solvent, the temperature of the resultant solution of WB$_6$ was lowered to 15° C. and the solution was stirred for 4 hours while maintaining the temperature of the solution at 15° C., to thereby recrystallize the WB$_6$. The recrystallized WB$_6$ was collected by suction filtration and dried, to thereby obtain 18.0 g of white crystals of WB$_6$.

The analysis of the obtained crystals of WB$_6$ by HPLC showed that the purity of the crystals of WB$_6$ was 100%.

Figure 3:
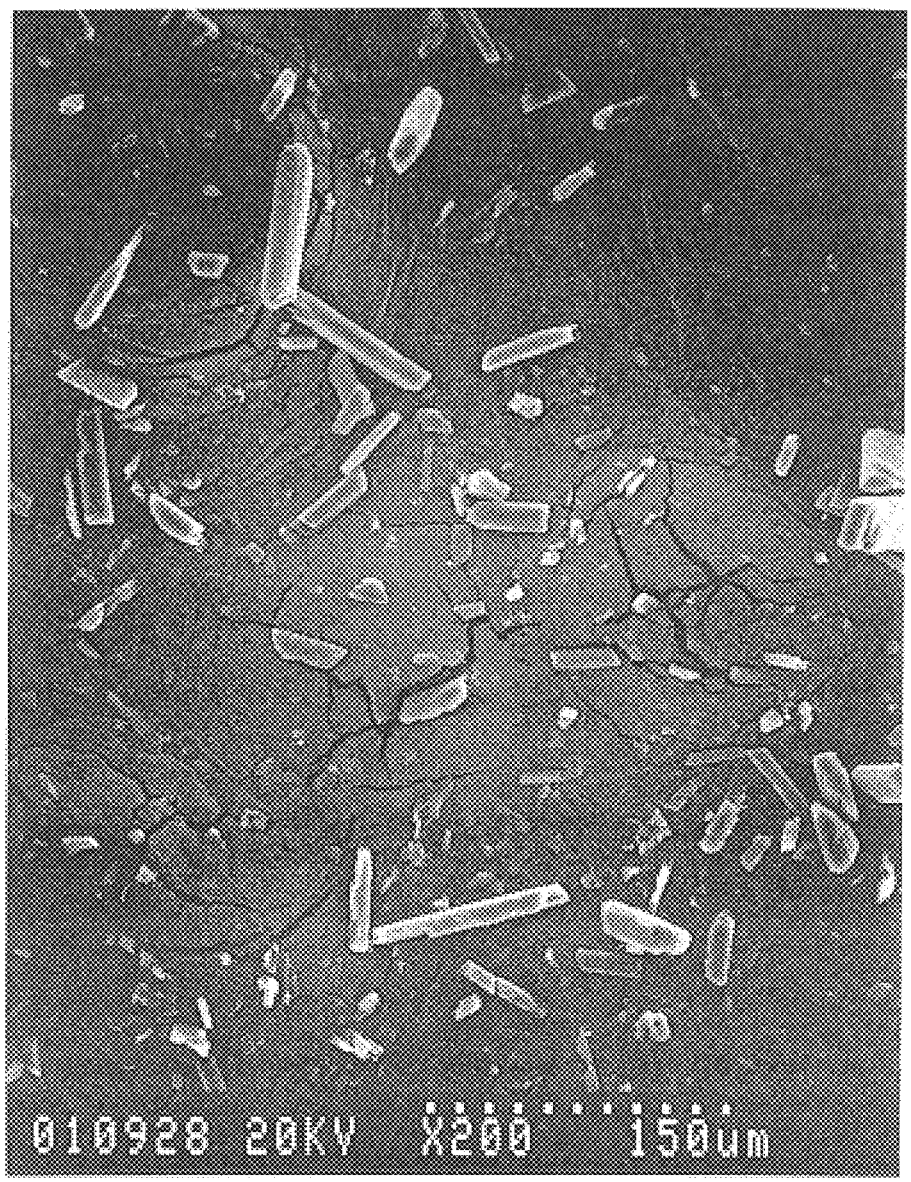
FIG. 3 is an SEM photomicrograph (×200) of the crystals of hexabenzylhexaazaisowurtzitane obtained in Reference Example 8 by subjecting the crude hexabenzylhexaazaisowurtzitane obtained in Reference Example 3 to recrystallization.

The crystals of WB$_6$ obtained above were examined by means of SEM to obtain a SEM photomicrograph (×200), and the obtained SEM photomicrograph is shown in FIG. 3. As is clearly seen from FIG. 3, each of the crystals of WB$_6$ had a clear needle-like shape, and the purity of the crystals of WB$_6$ was very high.

Reference Example 9
(Production of highly-purified WB$_6$ by an improved method.)

Into a 1-liter separable flask provided with a stirrer, a thermometer, a condenser and a dropping funnel were charged 514 ml of acetonitrile, 78 ml of distilled water, 117.9 g (1.1 mol) of benzylamine and 3.2 ml (0.055 mol) of acetic acid, and the resultant mixture in the flask was cooled to 20° C. by means of a constant temperature bath. Then, 36.28 g of a 40% aqueous solution of glyoxal (containing 0.25 mol of glyoxal) was gradually added to the mixture by means of the dropping funnel over 30 minutes while stirring and while maintaining the temperature of the mixture at 20° C. After the addition of the solution of glyoxal, the resultant mixture was heated to room temperature while stirring, and then, further stirred for 18 hours, to thereby effect a reaction. As a result, a white solid was deposited from the resultant yellow reaction mixture. The reaction mixture containing the white solid was subjected to suction filtration, to thereby collect the white solid, and then, the collected white solid was subjected to washing as follows. The collected wet white solid was dispersed in a mixed solvent of 170 ml of acetonitrile and 30 ml of distilled water, followed by stirring for 30 minutes, to thereby obtain a slurry. The obtained slurry was subjected to suction filtration to collect white needle-like shaped crystals. The obtained crystals were dried overnight at room temperature under reduced pressure, thereby obtaining 40.68 g of white needle-like crystals of WB$_6$. The analysis of the obtained crystals of WB$_6$ by HPLC showed that the purity of the crystals of WB$_6$ was 100%.

Figure 4:
FIG. 4 is an SEM photomicrograph (×200) of the crystals of hexabenzylhexaazaisowurtzitane obtained in Reference Example 9, wherein a washing treatment was conducted.

The white needle-like crystals of WB$_6$ obtained above was examined by means of a SEM to obtain a SEM photograph (×200), and the obtained SEM photomicrograph is shown in FIG. 4. As is clearly seen from FIG. 4, each of the crystals of WB$_6$ produced by an improved method had a clear needle-like shape, and the purity of WB$_6$ crystals was very high.

Reference Example 10

(Production of highly-purified $WB_6$ by an improved method.)

Production of $WB_6$ was conducted in substantially the same manner as in Reference Example 9, except that 235.8 g (2.2 mol) of benzylamine was used (instead of 117.9 g (1.1 mol)) and the temperature of the contents of the separable flask was 0° C. (instead of 20° C.), to thereby obtain 32.5 g of white needle-like crystals of $WB_6$. The analysis of the obtained crystals by HPLC showed that the purity of the crystals of $WB_6$ was 100%.

Reference Example 11

(Production of highly-purified $WB_6$ by an improved method.)

Production of $WB_6$ was conducted in substantially the same manner as in Reference Example 9, except that 85.7 g (0.8 mol) of benzylamine were used (instead of 117.9 g (1.1 mol)) and the temperature of the contents of the separable flask was 30° C. (instead of 20° C.), to thereby obtain 38.2 g of white needle-like crystals of $WB_6$. The analysis of the obtained crystals by HPLC showed that the purity of the crystals of $WB_6$ was 98.2%.

Reference Example 12

(Production of highly-purified $WB_6$ by an improved method.)

Production of $WB_6$ was conducted in substantially the same manner as in Reference Example 10, except that 4.8 ml (0.075 mol) of acetic acid were used (instead of 3.2 ml (0.055 mol)) and the 40% glyoxal aqueous solution was gradually added to the mixture by means of the dropping funnel over 6 hours (instead of 30 minutes) at 35° C. (instead of 20° C.), to thereby obtain 38.7 g of white needle-like crystals of $WB_6$. The analysis of the obtained crystals by HPLC showed that the purity of the crystals of $WB_6$ was 100%.

Reference Example 13

(Production of highly-purified $WB_6$ by an improved method.)

Into a 2-liter separable flask provided with a stirrer, a thermometer, a condenser and a dropping funnel were charged 1100 ml of acetonitrile, 100 ml of distilled water, 235.8 g (2.2 mol) of benzylamine and 12.8 ml (0.22 mol) of acetic acid, and the resultant mixture in the flask was cooled to 0° C. by means of a constant temperature bath. Then, 72.6 g of a 40% aqueous solution of glyoxal (containing 0.5 mol of glyoxal) was gradually added to the mixture by means of the dropping funnel over 2 hours while stirring and while maintaining the temperature of the mixture at 0° C. After the addition of the solution of glyoxal, the resultant mixture was heated to 25° C. while stirring, and then, further stirred for 18 hours, to thereby effect a reaction. As a result, a white solid was deposited from the resultant yellow reaction mixture. The reaction mixture containing the white solid was subjected to suction filtration to thereby collect the white solid, and then, the collected white solid was dispersed in a mixed solvent of 260 ml of acetonitrile and 40 ml of distilled water, followed by stirring for 30 minutes, to thereby obtain a slurry. The obtained slurry was subjected to suction filtration to collect white needle-like crystals. The obtained white needle-like crystals were dried overnight at room temperature under reduced pressure, thereby obtaining 71.6 g of white needle-like crystals of $WB_6$. The analysis of the obtained crystals of $WB_6$ by HPLC showed that the purity of the crystals of $WB_6$ was 99.3%.

EXAMPLE 18

(Method in which $WB_6$ (purity: 95% or more) obtained by an improved recrystallization method is used as a raw material.)

This Example 18 shows that the desired product can be obtained in very high yield when use is made of $WB_6$ having a purity of 95% or more, which is obtained by an improved recrystallization method.

0.41 g of 10% Pd—C (as a heterogeneous reduction catalyst) was charged into a 100 ml autoclave and the autoclave was purged with nitrogen gas. Then, hydrogen gas (as a reducing agent) was introduced into the autoclave so that the internal pressure of the autoclave became 2 kgf/cm². The contents of the autoclave were heated at 60° C. for 1 hour. A liquid mixture (maintained at 60° C.) obtained by dissolving 2.1 g of $WB_6$ (hexabenzylhexaazaisowurtzitane) (purity: 100%, obtained in Reference Example 8) in 30 ml of DMAC (as a solvent), followed by adding 1.84 g of acetic anhydride (as an acylating agent) to the resultant solution, was charged into the autoclave. Then, immediately, the stirring of the contents of the autoclave was started at a stirring rate of 700 rpm while maintaining the temperature at 60° C. and the pressure at 2 kgf/cm², and a reaction was performed for 1 hour, to thereby obtain a reaction mixture.

The analysis of the obtained reaction mixture by GC showed that the yields of $WA_4B_2$ (tetraacetyldibenzylhexaazaisowurtzitane) and $WA_4BH$ (tetraacetylbenzylhexaazaisowurtzitane) were 35% and 22%, respectively, (i.e., 57% in total) based on the $WB_6$, and the analysis of the reaction mixture by HPLC showed that the yield of $WA_4H_2$ (tetraacetylhexaazaisowurtzitane) was 24%, based on the $WB_6$.

EXAMPLE 19

(Method in which $WB_6$ (purity: 95% or more) produced by an improved method is used as a raw material.)

This Example shows that the desired product can be obtained in very high yield when use is made of $WB_6$ having a purity of 95% or more which is obtained by the method employed in the present invention.

A reaction was performed in substantially the same manner as in Example 18, except that the $WB_6$ (purity: 100%) obtained in Reference Example 9 was used, to thereby obtain a reaction mixture.

The analysis of the obtained reaction mixture by GC showed that the yields of $WA_4B_2$ and $WA_4BH$ were 37% and 22%, respectively, (i.e., 59% in total) based on the $WB_6$, and the analysis of the reaction mixture by HPLC showed that the yield of $WA_4H_2$ was 24% based on the $WB_6$.

Comparative Example 7

This Comparative Example shows that the yield of the desired products are markedly lowered when use is made of $WB_6$ having a purity of less than 95% which is produced and purified by the conventional methods.

A reaction was performed in substantially the same manner as in Example 18, except that the $WB_6$ (purity: 92.7%) obtained in Reference Example 4 was used and the reaction was performed for 4 hours (instead of 1 hour), to thereby obtain a reaction mixture.

The analysis of the obtained reaction mixture by GC and HPLC showed that the yield of the sum of $WA_4B_2$, $WA_4BH$ and $WA_4H_2$ was 10% or less, based on the $WB_6$.

EXAMPLE 20

(Method in which $WA_4B_2$ is produced with high selectivity.)

This Example shows that $WA_4B_2$ can be produced in high yield by controlling the reaction conditions, (particularly, by using a small amount of water-containing catalyst).

14.50 g of 10% Pd—C catalyst containing water (water content: 51.67%, catalyst content: 7.0 g) and 200 ml of DMAc were charged into a 2-liter autoclave, and the autoclave was purged with nitrogen gas. Then, hydrogen gas was introduced into the autoclave so that the internal pressure of the autoclave became 2 kgf/cm$^2$, and the contents of the autoclave were stirred at a stirring rate of 1000 rpm at 60° C. for 1 hour. The stirring rate and the internal pressure of the autoclave were lowered to 300 rpm and 1.1 kgf/cm$^2$, respectively, while maintaining the temperature at 60° C. 60 g of acetic anhydride were quickly charged into the autoclave by means of a syringe, and then, a solution (temperature: 60° C.) obtained by dissolving 70 g of WB$_6$ (hexabenzylhexaazaisowurtzitane) in 800 ml of DMAc was charged into the autoclave by means of a syringe. Then, immediately, the stirring rate and the internal pressure were elevated to 1000 rpm and 2 kgf/cm$^2$, respectively, while maintaining the temperature at 60° C., and a reaction was performed for 6 hours, to thereby obtain a reaction mixture.

The analysis of the obtained reaction mixture by GC showed that the yield of WA$_4$B$_2$ was 83%, based on the WB$_6$.

EXAMPLE 21

(Method in which WA$_4$H$_2$ is produced with high selectivity.)

0.42 g of 10% Pd—C was charged into a 100 ml autoclave, and the autoclave was purged with nitrogen gas. Then, hydrogen gas was introduced into the autoclave so that the internal pressure of the autoclave became 1.1 kgf/cm$^2$, and the contents of the autoclave were stirred at a stirring rate of 300 rpm at 60° C. for 1 hour. A solution obtained by dissolving 2.1 g of WB$_6$ and 1.82 g of acetic anhydride in 30 ml of DMAc was quickly charged into the autoclave. Then, immediately, the stirring rate and internal pressure were elevated to 2000 rpm and 2 kgf/cm$^2$, respectively, while maintaining the temperature at 60° C., and a reaction was performed for 5.5 hours, to thereby obtain a reaction mixture.

The analysis of the obtained reaction mixture by HPLC showed that the yield of WA$_4$H$_2$ was 75%, based on the WB$_6$, and neither WA$_4$B$_2$ nor WA$_4$BH was detected by the analysis of the reaction mixture by GC.

In this Example, the sample for HPLC analysis was prepared as follows. The reaction mixture (including the catalyst) was subjected to evaporation under a reduced pressure of 1 mmHg or less at 50° C., to thereby remove the liquid substances contained in the reaction mixture to obtain a residue. 60 ml of water were added to the residue under conditions such that there is no contact between the solids and air (i.e., oxygen), thereby obtaining a mixture. The obtained mixture was subjected to ultrasonication for 10 minutes by means of a ultrasonic cleaner, and subjected to filtration for removing the catalyst, to thereby obtain a filtrate. The obtained filtrate was used as a sample for HPLC analysis.

Industrial Applicability

By the method of the present invention, in the production of tetraacylhexaazaisowurtzitane derivatives (which are useful as precursors of a hexanitrohexaazaisowurtzitane utilized for improving the performance of conventional explosives) from a WB$_6$ by acylation, the decomposition of a hexaazaisowurtzitane skeleton, which is likely to occur at the initial stage of the acylation reaction of a WB$_6$ as a starting material, can be very effectively suppressed, so that desired tetraacylhexaazaisowurtzitane derivatives can be stably produced in high yield. Therefore, the method of the present invention is commercially advantageous. Further, the method of the present invention is also advantageous in that the lowering of the catalytic activity of the heterogeneous reduction catalyst during the reaction can be effectively suppressed, as compared to the case of conventional methods.

What is claimed is:

1. A method for acylating a hexakis(arylmethyl) hexaazaisowurtzitane by reductive dearylmethylation in the presence of an acylating agent, said hexakis(arylmethyl) hexaazaisowurtzitane being represented by the following formula (1):

WB$_6$          (1)

wherein each B independently represents a C$_7$–C$_{21}$ arylmethyl group, and W represents a hexavalent hexaazaisowurtzitane residue represented by the following formula (2):

(2)

which comprises contacting (a) a hexakis(arylmethyl) hexaazaisowurtzitane and (b) a heterogeneous reduction catalyst with each other in the presence of (c) an acylating agent and (d) hydrogen gas in (e) an amide group-containing solvent for said hexakis (arylmethyl)hexaazaisowurtzitane (a), thereby performing a reductive dearylmethylation/acylation reaction of said hexakis(arylmethyl) hexaazaisowurtzitane (a) to obtain a reaction mixture containing at least one tetraacylhexaazaisowurtzitane compound represented by the following formula (3):

WA$_4$B$_n$H$_{(2-n)}$          (3)

wherein n is an integer of 0 to 2, each A independently represents a C1–C10 acyl group, H represents a hydrogen atom, and each of B and W is as defined above, wherein there is no contact between said hexakis (arylmethyl)hexaazaisowurtzitane (a) and said heterogeneous reduction catalyst (b) in the absence of any of said acylating agent (c) and said hydrogen gas (d).

2. The method according to claim 1, wherein said reductive dearylmethylation/acylation reaction of said hexakis (arylmethyl)hexaazaisowurtzitane (a) is performed at 40 to 160° C.

3. The method according to claim 1 or 2, wherein said hexakis(arylmethyl)hexaazaisowurtzitane (a) and said solvent (e) are provided in the form of a solution of (a) in (e), and said heterogeneous reduction catalyst (b) and said hydrogen gas (d) are provided in the form of a mixture of (b) and (d), and wherein said solution of (a) in (e) is contacted with said mixture of (b) and (d) in the presence of said acylating agent (c).

4. The method according to claim 1 or 2, wherein said hexakis(arylmethyl)hexaazaisowurtzitane (a) and said solvent (e) are provided in the form of a solution of (a) in (e), and said heterogeneous reduction catalyst (b), said acylating agent (c) and said hydrogen gas (d) are provided in the form of a mixture of (b), (c) and (d), said mixture of (b), (c) and (d) being prepared by mixing said heterogeneous reduction catalyst (b) and said reducing agent (d), followed by addition of said acylating agent (c) thereto, and wherein said solution of (a) in (e) is contacted with said mixture of (b), (c) and (d).

* * * * *